US009109233B2

(12) United States Patent
Howley et al.

(10) Patent No.: US 9,109,233 B2
(45) Date of Patent: *Aug. 18, 2015

(54) RECOMBINANT POXVIRUS EXPRESSING HOMOLOGOUS GENES INSERTED

(75) Inventors: Paul Howley, Glen Waverly (AU); Sonja Leyrer, Munich (DE)

(73) Assignee: BAVARIAN NORDIC A/S, Kvistgaard (DK)

( * ) Notice: Subject to any disclaimer, the term of this patent is extended or adjusted under 35 U.S.C. 154(b) by 2155 days.

This patent is subject to a terminal disclaimer.

(21) Appl. No.: 11/985,510

(22) Filed: Nov. 15, 2007

(65) Prior Publication Data

US 2012/0135501 A1 May 31, 2012

Related U.S. Application Data

(63) Continuation of application No. 10/510,189, filed as application No. PCT/EP03/05047 on May 14, 2003, now Pat. No. 7,338,662.

(30) Foreign Application Priority Data

May 16, 2002 (DK) ................................ 2002 00752
May 16, 2002 (DK) ................................ 2002 00753

(51) Int. Cl.

*C12N 15/86* (2006.01)
*C07K 14/005* (2006.01)
*A61K 39/00* (2006.01)

(52) U.S. Cl.

CPC .............. *C12N 15/86* (2013.01); *C07K 14/005* (2013.01); *A61K 2039/5256* (2013.01); *A61K 2039/53* (2013.01); *C12N 2710/24122* (2013.01); *C12N 2710/24143* (2013.01); *C12N 2770/24122* (2013.01); *C12N 2840/20* (2013.01); *C12N 2840/203* (2013.01)

(58) Field of Classification Search

None
See application file for complete search history.

(56) References Cited

U.S. PATENT DOCUMENTS 5,093,258 A 3/1992 Cohen et al.
5,338,683 A 8/1994 Paoletti
5,494,807 A 2/1996 Paoletti et al.
5,514,375 A 5/1996 Paoletti et al.
5,635,369 A * 6/1997 Pompon et al. .............. 435/69.1
5,676,950 A 10/1997 Small et al.
5,744,141 A 4/1998 Paoletti et al.
5,891,442 A 4/1999 Paoletti et al.
6,217,882 B1 4/2001 Moyer et al.
6,893,845 B1 * 5/2005 Huse ............................... 506/14
7,338,662 B2 3/2008 Howley et al.
2004/0265324 A1 * 12/2004 Cardosa et al. ............ 424/186.1
2010/0173388 A1 * 7/2010 Howley et al. ............ 435/235.1
2011/0053259 A1 * 3/2011 Howley et al. ............ 435/320.1
2011/0053260 A1 * 3/2011 Howley et al. ............ 435/320.1

FOREIGN PATENT DOCUMENTS

WO 98/13500 A1 4/1998
WO 02/18585 A1 3/2002

OTHER PUBLICATIONS

Antoine et al., The Complete Genomic Sequence of the Modified Vaccinia Ankara Strain: Comparison with Other Orthopoxviruses, 1998, Virology, vol. 244, pp. 365-396.*
GenBank Accession M14931, Dengue virus type 4 polyprotein precursor, gene, complete cds, Feb. 15, 2000.*
GenBank Accession U88536, Dengue virus type 1 clone 45AZ5, complete genome, Sep. 19, 1997.*
GenBank Accession M19197, Dengue virus type 2 (S1 vaccine strain), complete genome, Aug. 2, 1993.*
Howley et al., Gene 172:233-237, 1996.
Howley et al., J. Virol. Methods79:65-74, 1999.
Men et al., Vaccine 18:2113-3122, 2000.
Ball, High-Frequency Homologous Recombination in Vaccinia Virus DNA, Journal of Virology vol. 61: 1788-1795 (1987).
Falkner et al., Transient Dominant Selection of Recombinant Vaccinia Viruses, Journal of Virology vol. 64: 3108-3111 (1990).
Scheiflinger et al., Transient marker stabilisation: a general procedure to construct marker-free recombinant vaccinia virus, Arch Virol (1998) 143: 467-474.
Gritz et al., Generation of Hybrid Genes and Proteins by Vaccinia Virus-Mediated Recombination: Application to Human Immunodeficiency Virus Type 1 env, Journal of Virology vol. 64: 5948-5957 (1990).

* cited by examiner

*Primary Examiner* — Benjamin P Blumel
(74) *Attorney, Agent, or Firm* — Law Office of Salvatore Arrigo and Scott, Lee, LLP

(57) ABSTRACT

The present invention relates to a recombinant poxvirus vector capable of expressing two or more homologous, foreign sequences, which derive from different variants of a microorganism, and which have a homology of 50% or above. The invention further relates to a method for preparing such recombinant poxvirus and the use of such recombinant poxvirus as medicament or vaccine. Additionally, a method for affecting preferably inducing, an immune response in a living animal, including a human, is provided.

22 Claims, 19 Drawing Sheets

SEQUENCE LISTING

```
<160> NUMBER OF SEQ ID NOS: 21

<210> SEQ ID NO 1
<211> LENGTH: 39
<212> TYPE: DNA
<213> ORGANISM: Artificial
<220> FEATURE:
```

-continued

<223> OTHER INFORMATION: Primer

<400> SEQUENCE: 1
cgcggatcca tgctgaacat cttgaacagg agacgcaga 39

<210> SEQ ID NO 2
<211> LENGTH: 21
<212> TYPE: DNA
<213> ORGANISM: Artificial
<220> FEATURE:
<223> OTHER INFORMATION: Primer

<400> SEQUENCE: 2
catgataaga gattgtatca g 21

<210> SEQ ID NO 3
<211> LENGTH: 80
<212> TYPE: DNA
<213> ORGANISM: Artificial
<220> FEATURE:
<223> OTHER INFORMATION: Primer

<400> SEQUENCE: 3
atgttgaaca taatgaacag gaggaaaaga tctgtgacca tgctcctcat gctgctgccc 60
acagccctgg cgttccatct 80

<210> SEQ ID NO 4
<211> LENGTH: 26
<212> TYPE: DNA
<213> ORGANISM: Artificial
<220> FEATURE:
<223> OTHER INFORMATION: Primer

<400> SEQUENCE: 4
gattttgcta ttcagtggac tggatg 26

<210> SEQ ID NO 5
<211> LENGTH: 48
<212> TYPE: DNA
<213> ORGANISM: Artificial
<220> FEATURE:
<223> OTHER INFORMATION: Primer

<400> SEQUENCE: 5
ccttaatcga attctcatgt catggatggg gtaaccagca ttaatagt 48

<210> SEQ ID NO 6
<211> LENGTH: 22
<212> TYPE: DNA
<213> ORGANISM: Artificial
<220> FEATURE:
<223> OTHER INFORMATION: Primer

<400> SEQUENCE: 6
gctcccattc aattcacatt gg 22

<210> SEQ ID NO 7
<211> LENGTH: 80
<212> TYPE: DNA
<213> ORGANISM: Artificial
<220> FEATURE:
<223> OTHER INFORMATION: Primer

<400> SEQUENCE: 7
atcccattcc tgaatgtggt gttaaagcta ctgagcgctt ctctcgtctc cgttctccgc 60
tctgggtgca tgtcccatac 80

<210> SEQ ID NO 8
<211> LENGTH: 22
<212> TYPE: DNA
<213> ORGANISM: Artificial
<220> FEATURE:
<223> OTHER INFORMATION: Primer

<400> SEQUENCE: 8
gtacatggat gatatagata tg 22

<210> SEQ ID NO 9
<211> LENGTH: 23
<212> TYPE: DNA
<213> ORGANISM: Artificial
<220> FEATURE:
<223> OTHER INFORMATION: Primer

<400> SEQUENCE: 9
gttgaaggat tcacttccgt gga 23

<210> SEQ ID NO 10
<211> LENGTH: 25
<212> TYPE: DNA
<213> ORGANISM: Artificial
<220> FEATURE:
<223> OTHER INFORMATION: Primer

<400> SEQUENCE: 10
gcattcacag attctattgt gagtc 25

<210> SEQ ID NO 11
<211> LENGTH: 26
<212> TYPE: DNA
<213> ORGANISM: Artificial
<220> FEATURE:
<223> OTHER INFORMATION: Primer

<400> SEQUENCE: 11
gtttcatcag aaatgactcc atgaaa 26

<210> SEQ ID NO 12
<211> LENGTH: 39
<212> TYPE: DNA
<213> ORGANISM: Artificial
<220> FEATURE:
<223> OTHER INFORMATION: Primer

<400> SEQUENCE: 12
cggggtaccc gacgaacaag gaactgtagc agaggcatc 39

<210> SEQ ID NO 13
<211> LENGTH: 38
<212> TYPE: DNA
<213> ORGANISM: Artificial
<220> FEATURE:
<223> OTHER INFORMATION: Primer

<400> SEQUENCE: 13
aactgcagtt gttcgtatgt cataaattct ttaattat 38

<210> SEQ ID NO 14
<211> LENGTH: 20
<212> TYPE: DNA

-continued

<213> ORGANISM: Artificial
<220> FEATURE:
<223> OTHER INFORMATION: Primer

<400> SEQUENCE: 14
caactctctt cttgattacc 20

<210> SEQ ID NO 15
<211> LENGTH: 19
<212> TYPE: DNA
<213> ORGANISM: Artificial
<220> FEATURE:
<223> OTHER INFORMATION: Primer

<400> SEQUENCE: 15
cgatcaaagt caatctatg 19

<210> SEQ ID NO 16
<211> LENGTH: 18
<212> TYPE: DNA
<213> ORGANISM: Artificial
<220> FEATURE:
<223> OTHER INFORMATION: Primer

<400> SEQUENCE: 16
gataccgatc acgttcta 18

<210> SEQ ID NO 17
<211> LENGTH: 18
<212> TYPE: DNA
<213> ORGANISM: Artificial
<220> FEATURE:
<223> OTHER INFORMATION: Primer

<400> SEQUENCE: 17
ggatatgatt atgtagag 18

<210> SEQ ID NO 18
<211> LENGTH: 21
<212> TYPE: DNA
<213> ORGANISM: Artificial
<220> FEATURE:
<223> OTHER INFORMATION: Primer

<400> SEQUENCE: 18
ctggataaat acgaggacgt g 21

<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
gacaattatc cgacgcaccg 20

<210> SEQ ID NO 20
<211> LENGTH: 24
<212> TYPE: DNA
<213> ORGANISM: Artificial
<220> FEATURE:
<223> OTHER INFORMATION: Primer

<400> SEQUENCE: 20
cgttagacaa cacaccgacg atgg 24

-continued

```
<210> SEQ ID NO 21
<211> LENGTH: 21
<212> TYPE: DNA
<213> ORGANISM: Artificial
<220> FEATURE:
<223> OTHER INFORMATION: Primer

<400> SEQUENCE: 21

cggatgaaaa atttttggaa g                                                21
```

RECOMBINANT POXVIRUS EXPRESSING HOMOLOGOUS GENES INSERTED

CROSS REFERENCE TO RELATED APPLICATIONS

Figure 1:
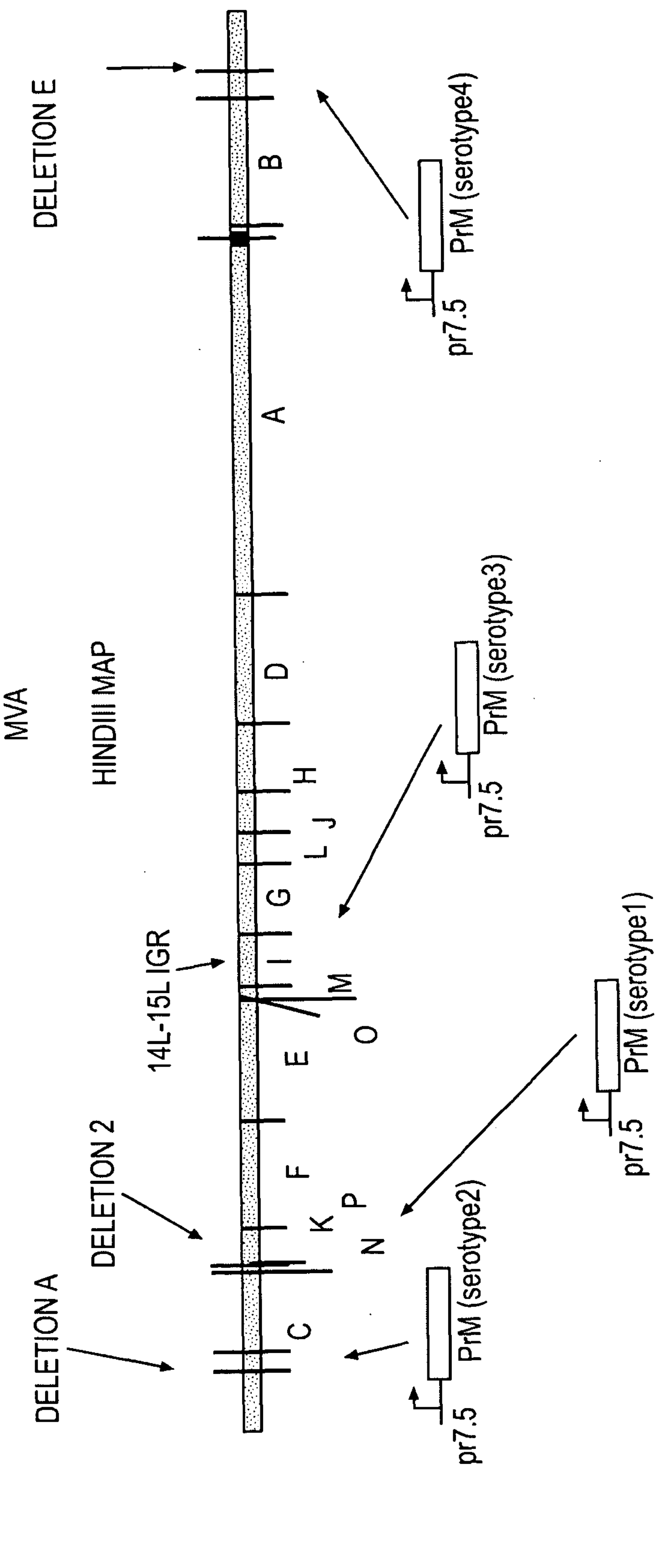
Figure 2:
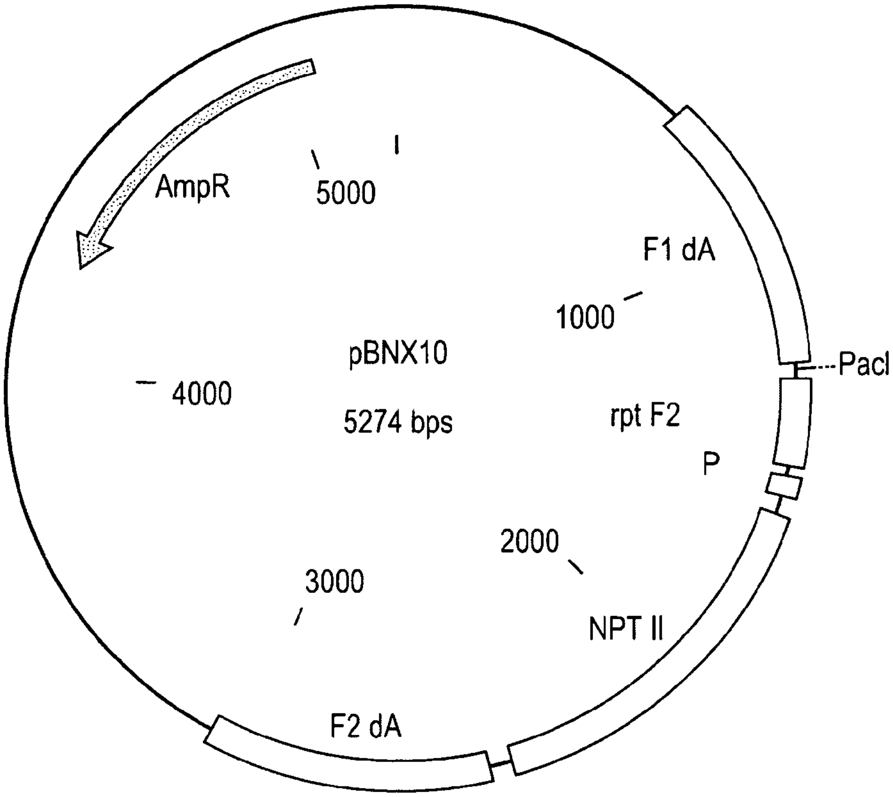
Figure 3:
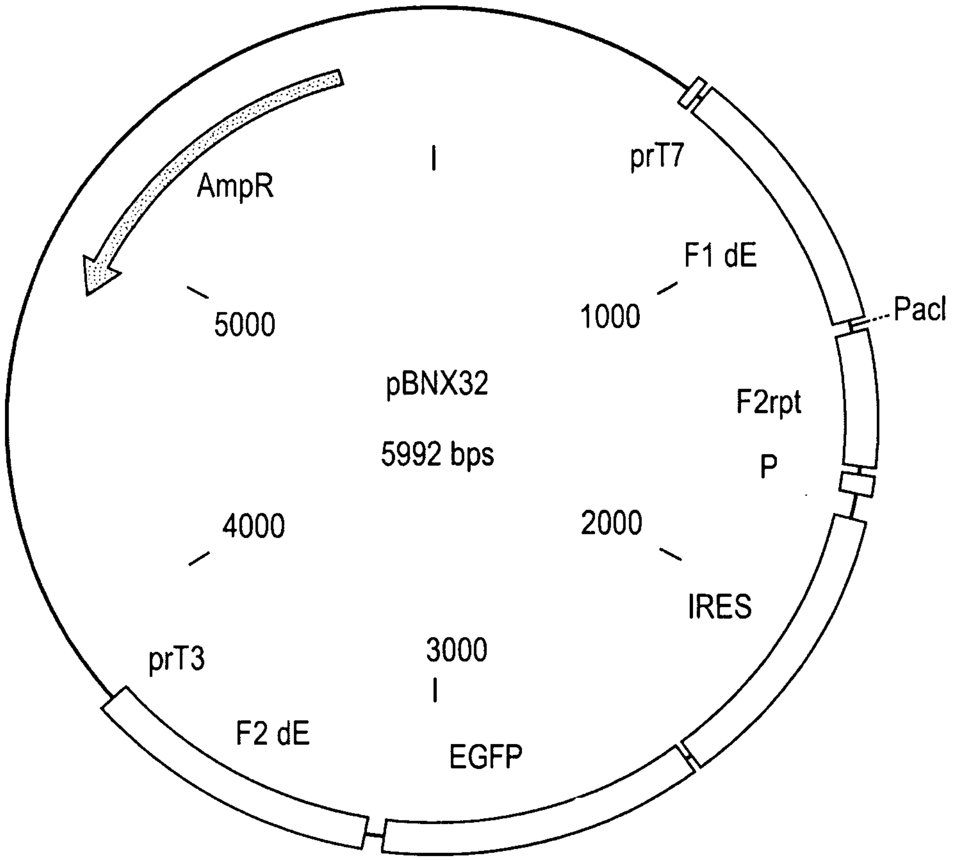
Figure 4:
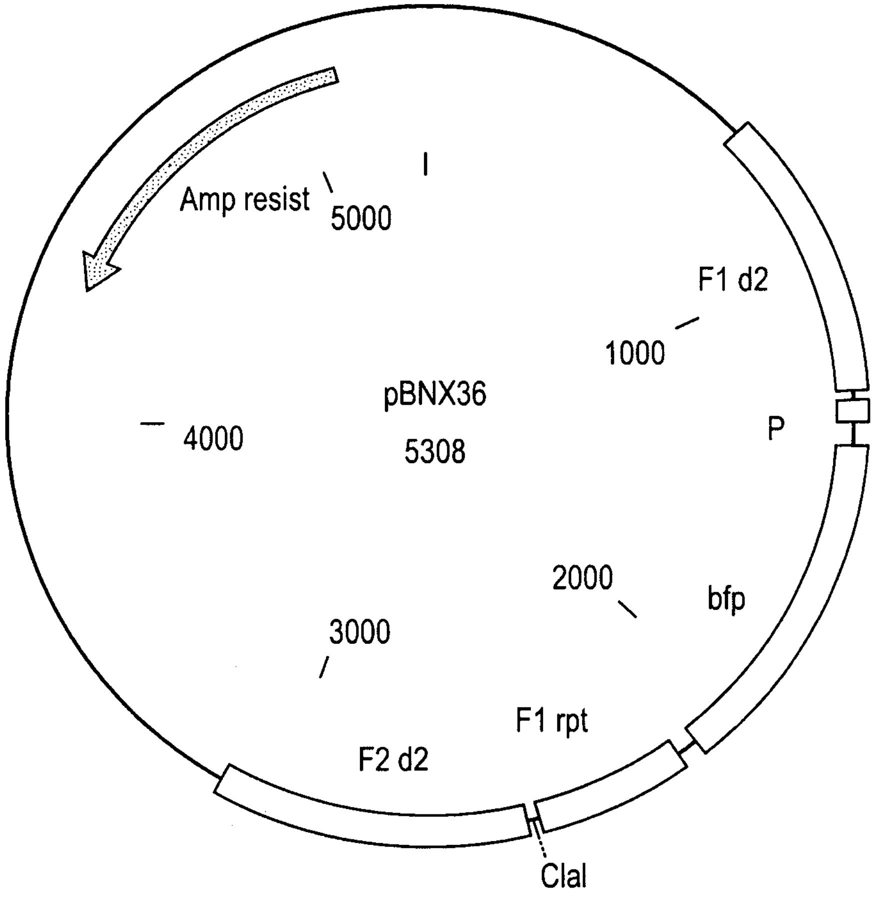
Figure 5:
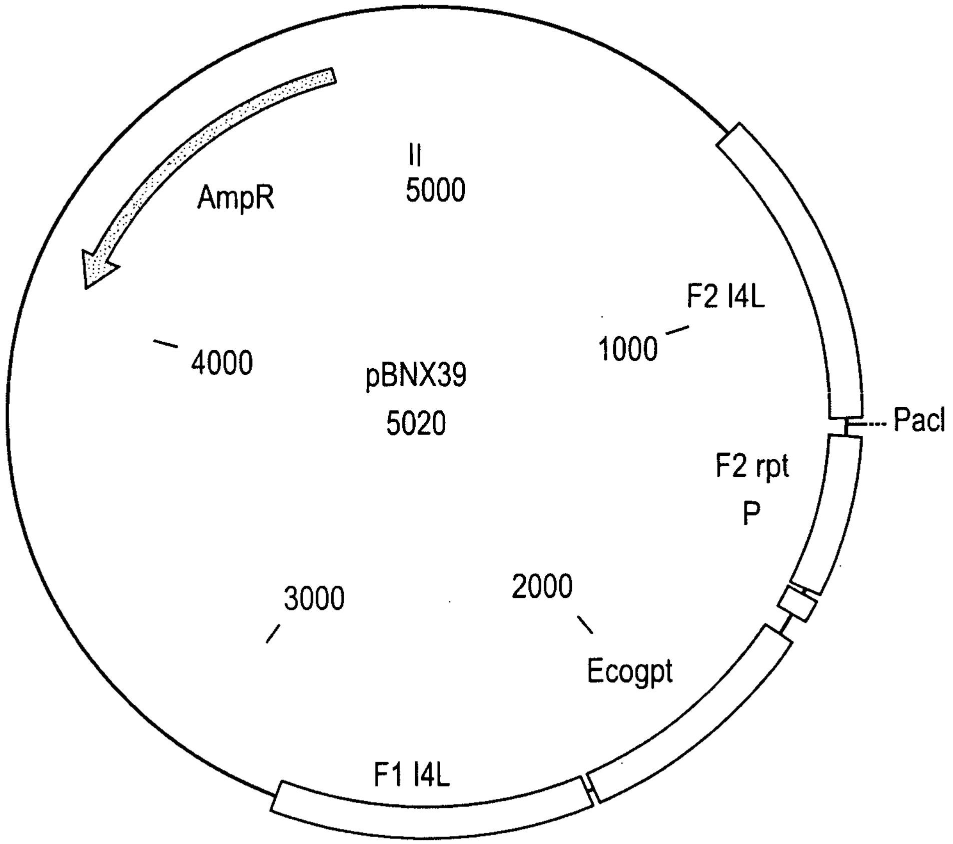

This application is a continuation of U.S. patent application Ser. No. 10/510,189 filed Sep. 30, 2004, now U.S. Pat. No. 7,338,662, which was filed as the U.S. national phase of PCT application PCT/EP03/05047, filed 14 May 2003, published 27 Nov. 2003 as WO 2003/097846, and claiming the priority of Danish patent application PA200200753 itself filed 16 May 2002 and Danish patent application PA200200752 itself filed 16 May 2002, whose entire disclosures are herewith incorporated by reference.

FIELD OF THE INVENTION

The present invention relates to a recombinant poxvirus capable of expressing two or more homologous foreign genes. Said genes are heterologous to the viral genome, but homologous in comparison to each other. The genes are especially derived from closely related variants or subtypes of a microorganism. The invention further relates to a method for preparing such recombinant poxvirus and to the use of such recombinant poxvirus as medicament or vaccine. Additionally, a method for affecting, preferably inducing, an immune response in a living animal, including a human, is provided.

BACKGROUND OF THE INVENTION

Every living organism is constantly challenged by infectious or pathogenous agents such as bacteria, viruses, fungi or parasites. The so-called immune system prevents the organism from permanent infections, diseases or intoxication caused by such agents.

The immune system of a mammal can be divided into a specific and an unspecific part although both parts are closely cross-linked. The unspecific immune response enables an immediate defense against a wide variety of pathogenic substances or infectious agents. The specific immune response is raised after a lag phase, when the organism is challenged with a substance for the first time. This specific immune response is mainly based on the production of antigen-specific antibodies and the generation of macrophages and lymphocytes, e.g. cytotoxic T-cells (CTL). The specific immune response is responsible for the fact that an individual who recovers from a specific infection is protected against this specific infection but still is susceptible for other infectious diseases. In general, a second infection with the same or a very similar infectious agent causes much milder symptoms or no symptoms at all. This so-called immunity persists for a long time, in some cases even lifelong. The underlying effect is often referred to as immunological memory, which can be used for vaccination proposes.

With the term vaccination a method is described, where an individual is challenged with a harmless, partial or inactivated form of the infectious agent to affect, preferably induce, an immunological response in said individual, which leads to long lasting—if not lifelong—immunity against the specific infectious agent.

The human smallpox disease is caused by Variola virus: Variola virus belongs to the family of Poxviridae, a large family of complex DNA viruses that replicate in the cytoplasma of vertebrate and invertebrate cells.

The family of Poxviridae can be divided into the two subfamilies Chordopoxvirinae and Entomopoxvirinae based on vertebrate and insect host range. The Chordopoxvirinae comprise beside others the genera of Orthopoxviruses and Avipoxviruses (Fields Virology, ed. by Fields B. N., Lippincott-Raven Publishers, 3rd edition 1996, ISBN: 0-7817-0253-4, Chapter 83).

The genera of Orthopoxviruses comprises variola virus, the causative agent of human smallpox, and also other viruses with economical importance, e.g. camelpox, cowpox, sheeppox, goatpox, monkeypox and Vaccinia virus. All members of this genus are genetically related and have similar morphology or host range. Restriction endonuclease maps have even shown high sequence identity from up to 90% between different members of the Orthopoxviruses (Mackett & Archard, [1979], J Gen Virol, 45: 683-701).

Vaccinia virus (VV) is the name given to the agent that was used at least the last 100 years for the vaccination against smallpox. It is not known whether VV is a new species derived from cowpox or variola virus by prolonged serial passages, the living representative of a now extinct virus or maybe a product of genetic recombination. Additionally, in course of the VV history, many strains of Vaccinia have arisen. These different strains demonstrate varying immunogenicity and are implicated to varying degrees with potential complications, the most serious of which is post-vaccinial encephalitis. However, many of these strains were used for the vaccination against smallpox. For example the strains NYCBOH, Western Reserve or Wyeth were used primarily in US, while the strain Ankara, Bern, Copenhagen, Lister and MVA were used for vaccination in Europe. As a result of the worldwide vaccination program with these different strains of VV in 1980 the WHO finally declared the successful eradication of variola virus.

Today, VV is mainly used as a laboratory strain, but beside this it is still considered as the prototype of Orthopoxviruses, which is also the reason why VV became one of the most intensively characterized viruses (Fields Virology, ed. by Fields B. N., Lippincott-Raven Publishers, 3rd edition 1996, ISBN: 0-7817-0253-4, Chapter 83 and 84).

VV and more recently other poxviruses have been used for the insertion and expression of foreign genes. The basic technique for inserting foreign genes into live infectious poxvirus involves recombination between pox DNA sequences flanking a foreign genetic element in a donor plasmid and homologous sequences present in the rescuing poxvirus. Genetic recombination is, in general, the exchange of homologous sections of DNA between two strands of DNA. In certain viruses RNA may replace DNA. Homologous sections of nucleic acid are sections of nucleic acid (DNA or RNA), which have the same sequence of nucleotide bases. Genetic recombination may take place naturally during the replication or manufacture of new viral genomes within an infected host cell. Thus, genetic recombination between viral genes may occur during the viral replication cycle that takes place in a host cell, which is co-infected with two or more different viruses or other genetic constructs. A section of DNA from a first genome is used interchangeably in constructing the section of the genome of a second co-infecting virus in which the DNA is homologous with that of the first viral genome.

Successful expression of the inserted DNA genetic sequence by the modified infectious virus requires two conditions. First, the insertion should be into a nonessential region of the virus in order that the modified virus remains viable. The second condition for expression of inserted DNA is the presence of a promoter in the proper relationship to the inserted DNA. Regularly, the promoter is located upstream from the DNA sequence to be expressed.

The usefulness of recombinant VV expressing, e.g., Hepatitis B virus surface antigen (HBsAg), Influenza virus hemagglutinin (InfHA) or *Plasmodium knowlesi* sporozoite antigen, as live vaccines for the prophylaxis of infectious diseases has been demonstrated and reviewed (Smith, et al. [1984] Biotechnology and Genetic Engineering Reviews 2, 383-407).

A further advantage of VV is the capacity to take up multiple foreign sequences, genes or antigens within a single VV genome (Smith & Moss [1983], Gene, 25(1): 21-28). Furthermore, it has been reported that it is possible to elicit immunity to a number of heterologous infectious diseases with a single inoculation of a polyvalent vaccine (Perkus et al., [1985], Science, Vol. 229, 981-984).

One example of the expression of various antigens by a single VV is described by Bray et al. It was shown that a recombinant VV, which is capable to express three different structural proteins of Dengue virus serotype 4, namely the capsid (C), pre-membrane (prM), envelope (E) protein, and two non-structural proteins of Dengue virus serotype 4, namely NS1 and NS2a, had the ability to protect mice against a homologous Dengue virus serotype 4 challenge (Bray et al., [1989], Virology 2853-2856).

The Dengue virus with its four serotypes, Dengue virus serotype 1 (Den-1) through Dengue virus serotype 4 (Den-4), is one important member of the *Flavivirus* genus with respect to infections of humans. Dengue virus infection produces diseases that range from flu-like symptoms to severe or fatal illness, Dengue haemorrhagic fever (DHF) with shock syndrome (DSS). Dengue outbreaks continue to be a major public health problem in densely populated areas of the tropical and subtropical regions, where mosquito vectors are abundant.

The concern over the spread of Dengue infection and other diseases induced by mosquito-borne *Flaviviruses* in many parts of the world has resulted in more efforts being made towards the development of Dengue vaccines, which could prevent both Dengue fever (DF), and Dengue haemorrhagic fever (DHF) and in vaccines useful to protect the vaccinated individual against infections induced by some or all mosquito-borne *flaviviruses*.

While most cases of DF are manifested after the first infection by any of the four serotypes, a large percentage of DHF cases occur in subjects who are infected for the second time by a serotype, which is different from the first infecting serotype of Dengue virus. These observations give rise to the hypothesis that sequential infection of an individual having antibodies against one Dengue serotype by a different virus serotype at an appropriate interval may result in DHF in a certain number of cases.

Accordingly, vaccination against one serotype does not result in a complete protection against Dengue virus infection, but only against infection with the same Dengue virus strain. Even more important, a person vaccinated against one serotype, has an increased risk of developing severe complications such as Dengue haemorrhagic fever when said person is infected from a Dengue virus strain of a different serotype.

Thus, a multivalent vaccine that contains antigens from all four Dengue virus serotypes is desired.

So far it had been suggested to prepare multivalent vaccines by mixing a panel of recombinant VV, each VV encoding sequences of a different viruses (Moss, [1990] Immunology, 2, 317-327). However, such a multivalent vaccine comprises several disadvantages. Firstly, it is cumbersome to generate several independent recombinant VV. Beside the separated production processes, also quality control and quality assurance is highly time consuming. Secondly, an infection with a mixture of recombinant viruses expressing different sequences always bears the risk that the infection event is not particularly well balanced. The main risk is that only individual recombinants, but not all different recombinants comprised in the multivalent vaccine will infect target cells. One reason might be an uneven distribution of recombinant viruses. Another reason might be interferences between the different recombinant viruses while infecting single cells. Such interferences are known as phenomenon of superinfection. In this case, only some antigens, but not all different antigens of the multivalent vaccine will finally be expressed from infected cells and, thus, presented to the immune system of a patient. As a consequence, immune protection will be obtained only against some of the antigens, but is far from providing a complete immune protection against the various antigens presented or presentable by the multivalent vaccine.

In the context of a vaccine against Dengue virus infection the approach of a multivalent vaccine has the disadvantage that if the different sequences are expressed in different amounts or in an unpredictable manner, as it had been shown for the envelope protein of Dengue virus 2 (Deuble et al., [1988], J. Virol 65: 2853), then such a vaccination is highly risky for a patient. An incomplete vaccination using a panel of recombinant Vaccinia viruses will only provide an immune protection against some, but not against all serotypes of Dengue virus. Unfortunately, in case of Dengue infection an incomplete vaccination is extremely unacceptable, since it increases the risk of lethal complications such as Dengue hemorrhagic fever.

OBJECT OF THE INVENTION

It is, therefore, an object of the present invention to provide a stable, effective and reliable vaccine against infectious diseases, which can be caused by more than one strain, clade, variant, subtype or serotype of said infectious disease causing microorganism.

It is a further object of the present invention to provide a stable, effective and reliable vaccine against Dengue virus infections, which allows reliable vaccination against all Dengue virus serotypes.

DETAILED DESCRIPTION OF THE INVENTION

The present invention is based on the idea to include into a poxvirus homologous genes derived from different strains, clades, variants, subtypes or serotypes of an infectious disease causing microorganism. As already mentioned above, there are, for example, 4 groups, subtypes or serotypes of Dengue virus existing which are all comprising the same types of genes as, e.g., the gene encoding the capsid (C) protein, the gene encoding the pre-membrane (PrM) or envelope (E) protein. However, the nucleic acid sequence of the same type of gene is not completely identical and not perfectly homologous, respectively, in all 4 serotypes: For example, sequence comparison (with Lasergene 4.05 Magalign, Macintosh) between the PrM genes of Dengue virus serotype 1, 2, 3 and 4 (PrM1-4) revealed a sequence identity of 66.5-72.9%, i.e., a homology of appr. 65-75%. It is assumed that differences and variations, respectively, in the genes of different subtypes of infectious disease causing microorganisms are the reasons why vaccination against one subtype does not automatically result in protection against infections with other variants of the same microorganism. It was, therefore, the idea to generate a recombinant virus including closely related or homologous genes derived from different strains, clades, variants, subtypes or serotypes of an infectious disease causing microorganism. However, as also already indicated above, homologous recombination between homologous sequences occur during the viral life cycle and even takes place between sections of DNA that are not perfectly homologous. It was, thus, expected that the insertion of homologous genes in a single viral genome would result in homologous recombination and, thus, in deletions of the inserted homologous genes.

However, when generating a recombinant poxvirus comprising in its genome at least two foreign genes with a homology of at least 60%, it was unexpectedly found that said homologous genes remain stably inserted into the viral genome.

Even if homologous genes, preferably with a homology of at least 50%, are inserted into different insertion sites of the viral genome, the genes also remain stably inserted into the viral genome: In this case, it was expected that recombination events between said homologous genes would additionally result in loss of viral genes important for amplification of the virus and for the viral life cycle, respectively, i.e., it was expected that the viral life cycle would seriously be damaged. Since, additionally, the frequency of recombination is proportional to the distance between two linked genes, it was expected that frequency of recombination events between two or more homologous genes located in different insertion sites would be high and, thus, result in deletions of said genes and/or in severe interferences. Accordingly, it was extremely surprising that no recombination events occurred, but that the homologous genes remained stably inserted into the different insertion sites of the viral genome.

According to the prior art, a recombinant poxvirus containing foreign DNA from *flavivirus*, such as Japanese Encaphalitis Virus (JEV), Yellow Fever Virus (YFV) and Dengue Virus, are known (U.S. Pat. No. 5,514,375). However, each gene derived from said *flaviviruses* were inserted only a single time and into the same insertion site. Additionally, sequence comparison with a suitable computer software (Lasergene 4.05 Megalign, Macintosh) revealed a homology of the genes inserted into the poxviral genome and derived from JEV of 20.2%-29.6%, from YFV of 29.2%-45.3%, and from Dengue Virus of 22.8%-29.5%.

Similar disclosure applies to WO 98/13500 describing insertion of Dengue virus antigens into the same insertion site of Modified Vaccinia Virus Ankara (MVA), especially into deletion site II.

U.S. Pat. No. 5,338,683 describes insertion of gp 13 and 14 of herpesvirus glycoprotein genes into two different insertion sites of a single recombinant poxvirus; however, both genes have a homology of 25.2% only.

Sequence comparison between influenza virus hemagglutinin and nucleoprotein gene inserted into the same insertion site (deletion site III) of a Modified Vaccinia Virus Ankara (MVA) resulted in a homology of 49.1% (U.S. Pat. No. 5,676,950; Sutter et al., [1994], Vaccine 12: 1032).

U.S. Pat. No. 5,891,442 discloses a recombinant poxvirus containing the coding sequence for the polyprotein VP2, VP3 and VP4 of infectious bursal disease. Said genes were fused and, thus, inserted into a single insertion site and have a homology of 41.9%-50.3%.

Finally, U.S. Pat. No. 6,217,882 describes a recombinant swinepox virus vector containing pseudorabies antigens gp50 and gp63 with a homology of 52.7% inserted into the same insertion site.

In summary, it can be stated that according to the prior art homologous genes or sequences having a homology of at least 50% are all inserted into the same or a single insertion site within the viral genome.

According to the present invention, homologous genes or sequences have a homology of at least 50%, i.e., a homology of 50%-100%, i.e., at least 50% identical nucleotide bases. Genes or sequences having a homology below 50% can be considered as being heterologous. In the context of the present invention, the term "homologous" or "homology" is used when genes or sequences are compared to each other, whereas the terms "foreign" gene, "exogenous" or "heterologous" sequence are used when genes or sequences are compared to the poxviral genome; i.e., said terms refer to a DNA sequence which is in nature not normally found associated with a poxvirus as used according to the invention. Accordingly, the present invention relates to a recombinant poxvirus comprising at least two genes which are heterologous in comparison to the viral genome, but which are homologous among each other. The term "genes" refers to coding sequences, which encode, e.g., proteins, polypeptides, peptides, antigens and the like. Proteins, polypeptides or peptides translated from homologous genes fulfill the same tasks and show the same functional properties. Homologous genes are regularly derived from different, but related sources or organisms. According to one embodiment of the present invention, the homology in the coding sequences is preferably 70% to 80%, more preferably 80% to 90% or 90% to 100%. Most preferred is a homology of 65% to 75%.

Since the recombinant poxvirus according to the present invention comprises the relevant genetic information in one single infectious unit or in one virus particle only, there is no risk of uneven infection and unbalanced expression of the different homologous sequences. Thus, the recombinant poxvirus according to the present invention comprising and capable of expressing several closely or even closest related genes or almost identical sequences in one infected cell is particularly advantageous for the generation of multivalent vaccines.

This advantage is particularly interesting for the development of vaccines against diseases, which can be caused by several closely related strains or serotypes of a virus, like e.g. Dengue virus. Recombinant poxviruses comprising homologous genes of different Dengue virus serotypes are described in the Examples.

The homologous genes or sequences according to the present invention can be derived from any microorganism, such as any virus except the vector virus, any bacterium, any fungus or parasite. Preferably, the homologous genes or sequences are derived from an infectious or pathogenic microorganism and most preferably from different strains or clades, variants, subtypes or serotypes of said microorganism.

The terms "strain" or "clade" are technical terms, well known to the practitioner, referring to the taxonomy of microorganisms. The taxonomic system classifies all so far charactersed microorganisms into the hierarchic order of Families, Genera, species, strains (Fields Virology, ed. by Fields B. N., Lippincott-Raven Publishers, 4$^{th}$ edition 2001). While the criteria for the members of Family is their phylogenetic relationship, a Genera comprises all members which share common characteristics, and a species is defined as a polythetic class that constitutes a replicating lineage and occupies a particular ecological niche. The term "strain" or "clade" describes a microorganism, i.e. virus, which shares the common characteristics, like basic morphology or genome structure and organisation, but varies in biological properties, like host range, tissue tropism, geographic distribution, attenuation or pathogenicity. The term "variants" or "serotypes" further distinguishes between members of the same strain, also called subtypes, which show individual infection spectra or antigenic properties due to minor genomic variations.

According to a further embodiment of the present invention the homologous genes or sequences are selected from viruses, preferably viruses, which belong to the genera of *Flaviviruses*, such as preferable—but not limited to—Dengue virus, West Nile virus or Japanese encephalitis virus; which belong to the genera of Retroviruses, such as preferable—but not limited to—Human Immunodeficiency Virus (HIV); which belong to the genera of Enteroviruses, such as preferable—but not limited to—Hand, Foot and Mouth disease, EV71; which belong to the genera of Rotaviruses or which belong to the genera of Orthomyxoviruses, such as preferable—but not limited to—Influenza virus. Most preferred are homologous genes derived from a *Flavivirus*.

According to a further preferred embodiment, the homologous genes are selected from Dengue virus genes, preferably C, NS1 and/or NS2, or preferably E, more preferably PrM. Most preferred are homologous genes derived from different serotypes of the virus, wherein said genes may be derived from one, two, three or from all of the 4 Dengue virus serotypes.

According to still a further embodiment the homologous genes are selected from different HIV stains or clades. Preferably the homologous genes are selected from the gag/pol coding sequence, more preferably from the env coding sequence or further preferably from a combination of structural and/or regulatory HIV coding sequences.

The vector virus suitable for the present invention is selected from the group of poxviruses, which can be easily cultured in selected host cells as, e.g., avian host cells, but which are highly replication deficient or actually not replicating in humans or human cells.

According to some preferred embodiments the poxvirus according to the present invention is selected from the group comprising canarypox viruses (Plotkin et al. [1995] Dev Biol Stand. vol 84: pp 165-170. Taylor et al. [1995] Vaccine, Vol 13. No. 6: pp 539-549), fowlpox viruses (Afonso et al. [2000] J Virol, pp 3815-3831. Fields Virology, ed. by Fields B. N., Lippincott-Raven Publishers, 4$^{th}$ edition 2001, Chapter 85: page 2916), penguin pox viruses (Stannard et al. [1998] J Gen Virol, 79, pp 1637-1649) or derivatives thereof. Since these viruses belong to the genera of Avipoxviruses they can be easily cultured and amplified in avian cells. However, in mammalian or human cells they are replication defective, which means that essentially no or nearly no infectious progeny viruses are produced.

According to a further embodiment of the present invention a Vaccinia virus, preferably an attenuated Vaccinia virus, is used for the generation of recombinant poxviruses comprising two or more homologous genes.

Although it is known that Vaccinia viruses (VV) may undergo homologous recombination of short homologous sequences and thereby may delete homologous sequences (Howley et al., [1996], Gene 172: 233-237) the inventors provide a recombinant Vaccinia virus including homologous sequences or genes stably inserted into its genome. This finding is particularly unexpected, since according to Howely et al. already short sequences from up to 300 base pairs (bp) were sufficient to induce genomic rearrangement and deletion of homologous sequences in Vaccinia virus. The practitioner would, thus, expect that longer sequences would induce recombination events with an even higher probability. However, according to the present invention even sequences comprising complete homologous genes can be stably inserted into the genome of Vaccinia virus.

One—not limiting—example of a vaccinia virus is the highly attenuated and host range restricted Vaccinia strain, Modified Vaccinia Ankara (MVA) (Sutter, G. et al. [1994], Vaccine 12: 1032-40): MVA has been generated by about 570 serial passages on chicken embryo fibroblasts of the Ankara strain of Vaccinia virus (CVA) (for review see Mayr, A., et al. [1975], Infection 3, 6-14). As a consequence of these long-term passages CVA deleted about 31 kilobases of its genomic sequence. The resulting virus strain, MVA, was described as highly host cell restricted (Meyer, H. et al., J. Gen. Virol. 72, 1031-1038 [1991]). A typical MVA strain is MVA 575 that has been deposited at the European Collection of Animal Cell Cultures under the deposition number ECACC V00120707.

In another embodiment the MVA-Vero strain or a derivative thereof can be used according to the present invention. The strain MVA-Vero has been deposited at the European Collection of Animal Cell Cultures under the deposition number ECACC V99101431 and ECACC 01021411. The safety of the MVA-Vero is reflected by biological, chemical and physical characteristics as described in the International Patent Application PCT/EP01/02703. In comparison to normal MVA, MVA-Vero has one additional genomic deletion.

The term "derivatives" of a virus according to the present invention refers to progeny viruses showing the same characteristic features as the parent virus but showing differences in one or more parts of its genome.

Still another embodiment according to the present invention uses MVA-BN. MVA-BN has been deposited at the European Collection of Animal Cell Cultures with the deposition number ECACC V00083008. bp using MVA-BN or a derivative thereof a particular safe virus vaccine is generated, since it has been shown that the MVA-BN virus is an extremely high attenuated virus, derived from Modified Vaccinia Ankara virus. Therefore, in the most preferred embodiment, MVA-BN or derivatives thereof containing two or more homologous genes according to the present invention is used as viral vector. The term "derivative of MVA-BN" describes a virus, which has the same functional characteristics compared to MVA-BN. The features of MVA-BN, the description of biological assays allowing the evaluation whether an MVA is MVA-BN and a derivative thereof and methods allowing the generation of MVA-BN or derivatives thereof are described in WO 02/42480 (incorporated herein by reference). One easy way to examine a functional characteristic of MVA-BN or derivatives thereof is its attenuation and lack of replication in human HaCat cells.

In a recombinant poxvirus according to the present invention the expression of the exogenous sequences is controlled preferably by a poxviral transcriptional control element, more preferably by an MVA, canary pox, fowl pox, or penguin pox transcriptional control element or most preferably a Vaccinia virus promoter. Poxviral transcriptional control elements according to the present invention comprise furthermore every transcriptional control element functional in a poxviral system.

The insertion of the exogenous sequences according to the present invention is preferably directed into a non-essential region of the virus genome. Non-essential regions are e.g. loci or open reading frames (ORF) of poxviral genes, which are non-essential for the poxviral life cycle. Also intergenic regions, which describe the space inbetween two ORF, are considered as non-essential regions according to the present invention. In another embodiment of the invention, the exogenous sequences are inserted at a naturally occurring deletion site of the MVA genome (disclosed in PCT/EP96/02926 and incorporated herein by reference).

The orientation of the inserted DNA does not have an influence on the functionality or stability of the recombinant virus according the present invention.

Since the recombinant poxvirus according to the invention is highly growth restricted and, thus, highly attenuated, it is an ideal candidate for the treatment of a wide range of mammals including humans and even immune-compromised humans. Hence, the present invention also provides a pharmaceutical composition and also a vaccine for inducing an immune response in a living animal body, including a human.

The pharmaceutical composition may generally include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of vaccines, the recombinant poxvirus according to the invention is converted into a physiologically acceptable form. This can be done based on the experience in the preparation of poxvirus vaccines used for vaccination against smallpox (as described by Stickl, H. et al. [1974] Dtsch. med. Wschr. 99, 2386-2392). For example, the purified virus is stored at ~80° C. with a titre of 5×10E8 $TCID_{50}$/ml formulated in about 10 mM Tris, 140 mM NaCl pH 7.4. For the preparation of vaccine shots, e.g., 10E2-10E8 particles of the virus are lyophilized in 100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g. human serum albumin) suitable for in vivo administration. The glass ampoule is then sealed and can be stored between 4° C. and room temperature for several months. However, as long as no need exists the ampoule is stored preferably at temperatures below −20° C.

For vaccination or therapy the lyophilisate can be dissolved in 0.1 to 0.5 ml of an aqueous solution, preferably physiological saline or Tris buffer, and administered either systemically or locally, i.e. parenteral, subcutaneous, intravenous, intramuscular, by scarification or any other path of administration know to the skilled practitioner. The mode of administration, the dose and the number of administrations can be optimized by those skilled in the art in a known manner. However, most commonly a patient is vaccinated with a second shot about one month to six weeks after the first vaccination shot.

The recombinant virus according to the present invention is used for the introduction of the exogenous coding sequences into a target cell. The introduction of an exogenous coding sequence into a target cell may be used to produce in vitro proteins, polypeptides, peptides, antigens and epitopes, respectively. Furthermore, the method for introduction of a homologous or of a heterologous sequence into cells may be applied for in vitro and in vivo therapy. For in vitro therapy, isolated cells that have been previously (ex vivo) infected with the recombinant poxvirus according to the invention are administered to the living animal body for inducing an immune response. For in vivo therapy, the recombinant poxvirus according to the invention is directly administered to the living animal body for inducing an immune response. In this case, the cells surrounding the site of inoculation are directly infected in vivo by the virus or its recombinant according to the invention. After infection, the cells synthesize the proteins, polypeptides, peptides or antigens, which are encoded in the exogenous coding sequences and, subsequently, present them or parts thereof on the cellular surface. Specialized cells of the immune system recognize the presentation of such foreign proteins, polypeptides, peptides, antigens and epitopes and launch a specific immune response.

Methods to obtain recombinant poxviruses or to insert exogenous coding sequences into a poxviral genome are well known to the person skilled in the art. Additionally, the method is described in the examples and can also be deduced or completed from the following references:

*Molecular Cloning*, A laboratory Manual. Second Edition. By J. Sambrook, E. F. Fritsch and T. Maniatis. Cold Spring Harbor Laboratory Press. 1989: describes techniques and know how for standard molecular biology techniques such as cloning of DNA, DNA and RNA isolation, western blot analysis, RT-PCR and PCR amplification techniques.

*Virology Methods Manual*. Edited by Brian W J Mahy and Hillar O Kangro. Academic Press. 1996: describes techniques for the handling and manipulation of viruses.

*Molecular Virology*: A Practical Approach. Edited by A J Davison and R M Elliott. The Practical Approach Series. IRL Press at Oxford University Press. Oxford 1993. Chapter 9: Expression of genes by Vaccinia virus vectors.

*Current Protocols in Molecular Biology*. Publisher: John Wiley and Son Inc. 1998. Chapter 16, section IV: Expression of proteins in mammalian cells using Vaccinia viral vector: describes techniques and know-how for the handling, manipulation and genetic engineering of MVA.

For the generation of recombinant poxviruses according to the present invention different methods may be applicable: The DNA sequence to be inserted into the virus may be placed into an *E. coli* plasmid construct into which DNA homologous to a section of DNA of the poxvirus has been inserted. Separately, the DNA sequence to be inserted is ligated to a promoter. The promoter-gene linkage is positioned in the plasmid construct so that the promoter-gene linkage is flanked on both ends by DNA homologous to a DNA sequence flanking a region of pox DNA containing a non-essential locus. The resulting plasmid construct is amplified by growth within *E. coli* bacteria and isolated. The isolated plasmid containing the DNA gene sequence to be inserted is transfected into a cell culture, e.g., chicken embryo fibroblasts (CEFs), along with the poxvirus. Recombination between homologous pox DNA in the plasmid and the viral genome, respectively, gives a poxvirus modified by the presence of foreign DNA sequences.

According to a more preferred embodiment, a cell of a suitable cell culture as, e.g., CEF cells, is infected with a poxvirus. The infected cell is, subsequently, transfected with a first plasmid vector comprising the foreign gene, preferably under the transcriptional control of a poxvirus expression control element. As explained above, the plasmid vector also comprises sequences capable of directing the insertion of the exogenous sequence into a selected part of the poxviral genome. Optionally, the plasmid vector contains also a cassette comprising a marker and/or selection gene operably linked to a poxviral promoter. Suitable marker or selection genes are, e.g., the genes encoding the Green Fluorescent Protein, β-Galactosidase, neomycin, phosphoribosyltransferase or other markers. The use of selection or marker cassettes simplifies the identification and isolation of the generated recombinant poxvirus. However, a recombinant poxvirus can also be identified by PCR technology. Subsequently, a further cell is infected with the recombinant poxvirus obtained as described above and transfected with a second vector comprising a gene, which is homologous to the gene included in the first vector. In case, this gene shall be included into a different insertion site of the poxviral genome, the second vector also differs in the sequence directing the integration of the homologous gene into the genome of the poxvirus. After homologous recombination occurred, the recombinant virus comprising two homologous genes can be isolated. For introducing more than two homologous genes into the recombinant virus, the steps of infection and transfection are repeated by using the recombinant virus isolated in previous steps for infection and by using a further vector comprising a further homologous gene for transfection.

Alternatively, the steps of infection and transfection as described above are interchangeable, i.e., a suitable cell may at first be transfected by the plasmid vector comprising the foreign gene and, then, infected with the poxvirus.

As a further alternative, it is also possible to introduce each homologous gene into different viruses, coinfect a cell with all the obtained recombinant viruses and screen for a recombinant including all homologous genes.

The invention further provides a kit comprising two or more plasmid vector constructs capable of directing the integration of expressible, homologous genes into the poxvirus genome. Beside a suitable cloning site such plasmid vectors comprise sequences capable of directing the insertion of the exogenous sequence to selected parts in the poxviral genome. Optionally, such vectors comprise selection or marker gene cassettes. The kit further comprises means and instructions to select viruses, which are recombinant for one or several of the homologous genes and optionally a selection or marker gene, inserted via said vector constructs.

According to another further embodiment the invention includes DNA sequences or parts thereof derived from or homologous to the recombinant poxvirus of the present invention. Such sequences comprise at least part of the exogenous sequence comprising at least a fragment of one of the homologous gene according to the present invention and at least a fragment of the genomic poxvirus sequence according to the present invention, said genomic poxvirus sequences preferably flanking the exogenous sequence.

Such DNA sequences can be used to identify or isolate the virus or its derivatives, e.g. by using them to generate PCR-primers, hybridization probes or in array technologies.

SHORT DESCRIPTION OF THE FIGURES

FIG. 1: Schematic presentation of the insertion sites of the four PrM (=pre-membrane) genes (serotype 1-4) in the MVA genome according to Example 1.

FIGS. 2-9 and 12-17: Insertion plasmid vector constructs indicating the name of the vector, its size and the localization of the sequences of interest such as: AmpR=ampicillin resistance gene, bfp=blue florescence protein gene, dA=deletion A, dE=deletion E, d2=deletion 2, Ecogpt=*E. coli* guanosin-phosphoribosyl-transferase gene, EGFP=enhanced green florescence protein gene, F1=flanking sequence 1, F2=flanking sequence 2, I4L=intergenic region I4L, IGR=intergenic region, NPT II=neomycin resistance gene, P=poxvirus promoter, pr7.5=Vaccinia promoter 7.5, PrM=pre-membrane gene of Dengue virus, number indicating from which of the four serotypes it derives, rpt=repetition of flanking sequence.

Figure 10:
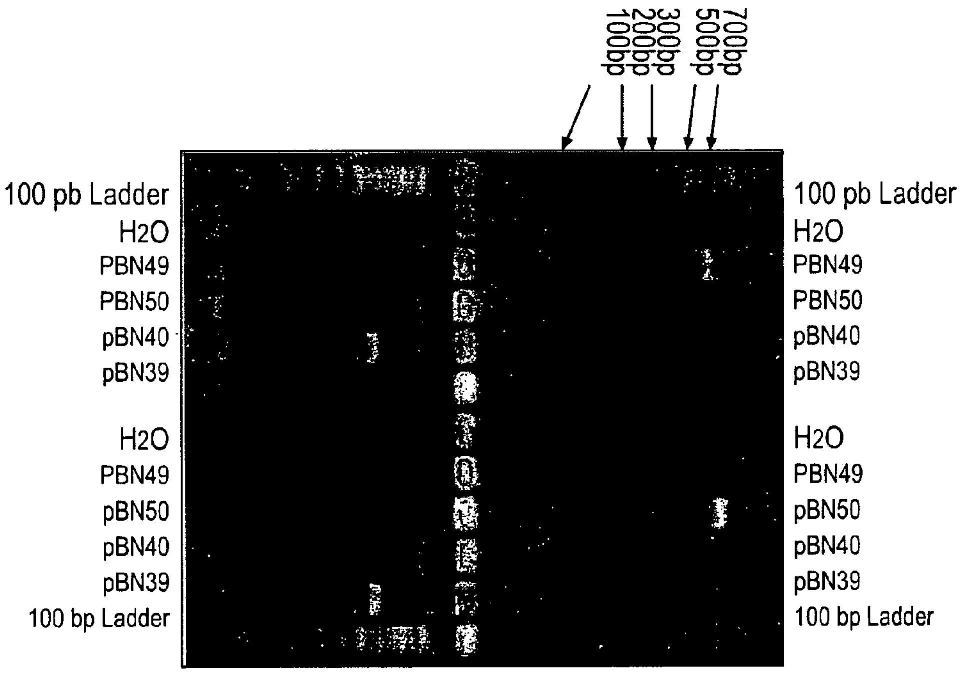

FIG. 10: PCR verification of the vector cloning strategies of four different insertion vectors (pBN49, pBN50, pBN40, pBN39). Each of the plasmids was tested with 4 different PCR primer combinations. Each combination is specific for one distinct PrM sequence integrated into one distinct insertion site.

Figure 11:
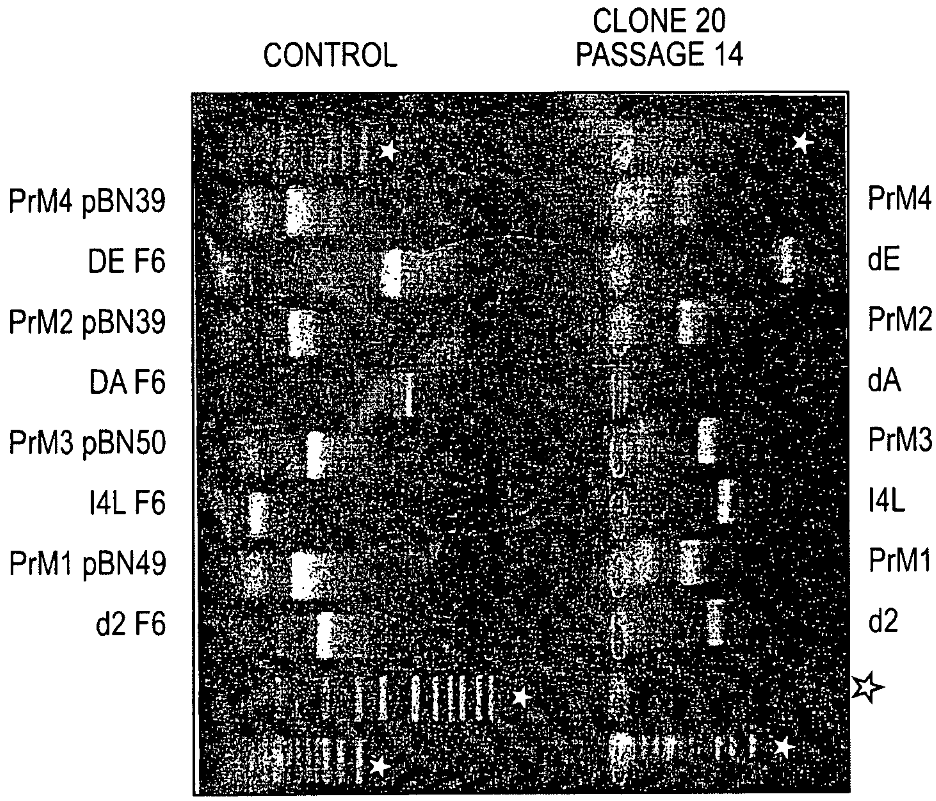
Figure 12:
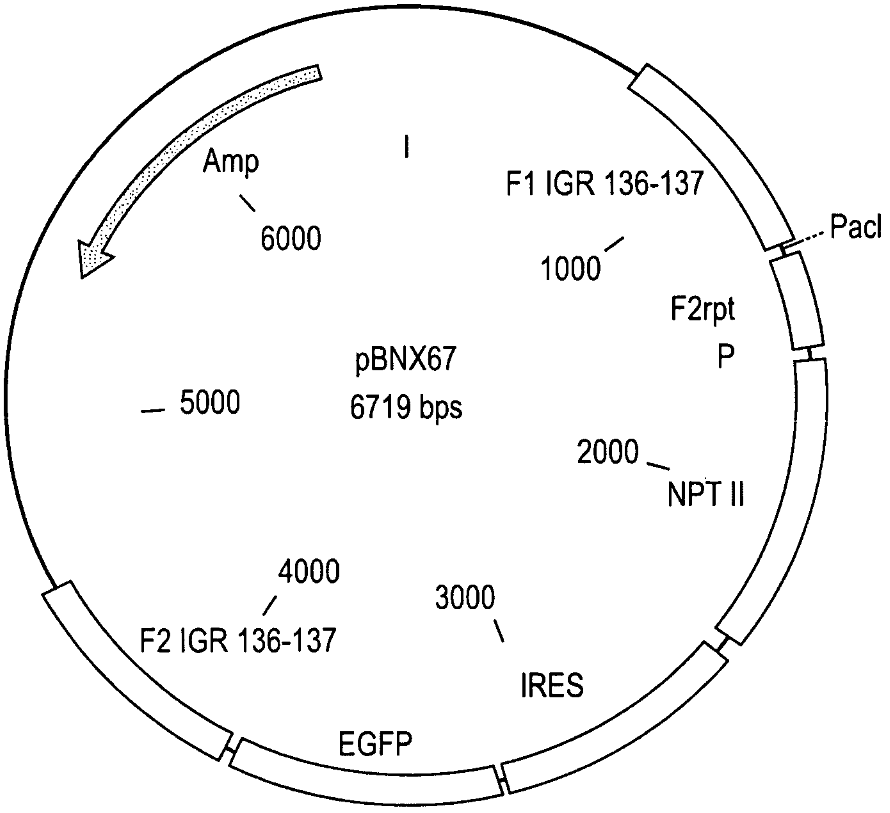
Figure 13:
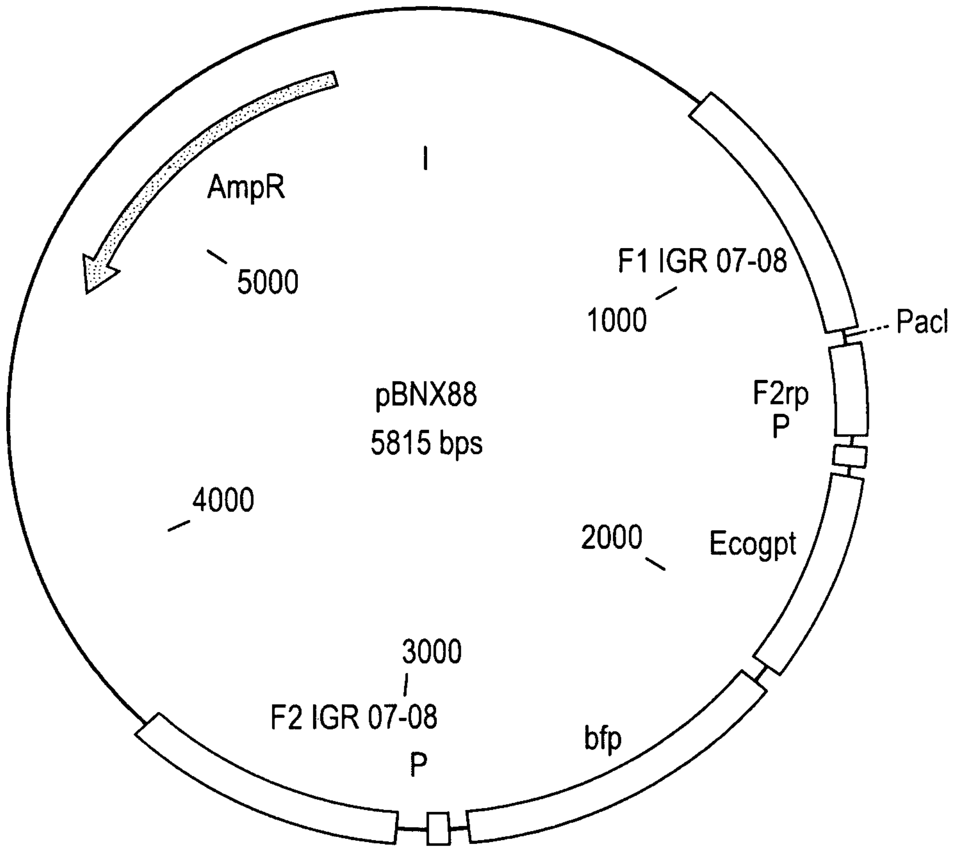
Figure 14:
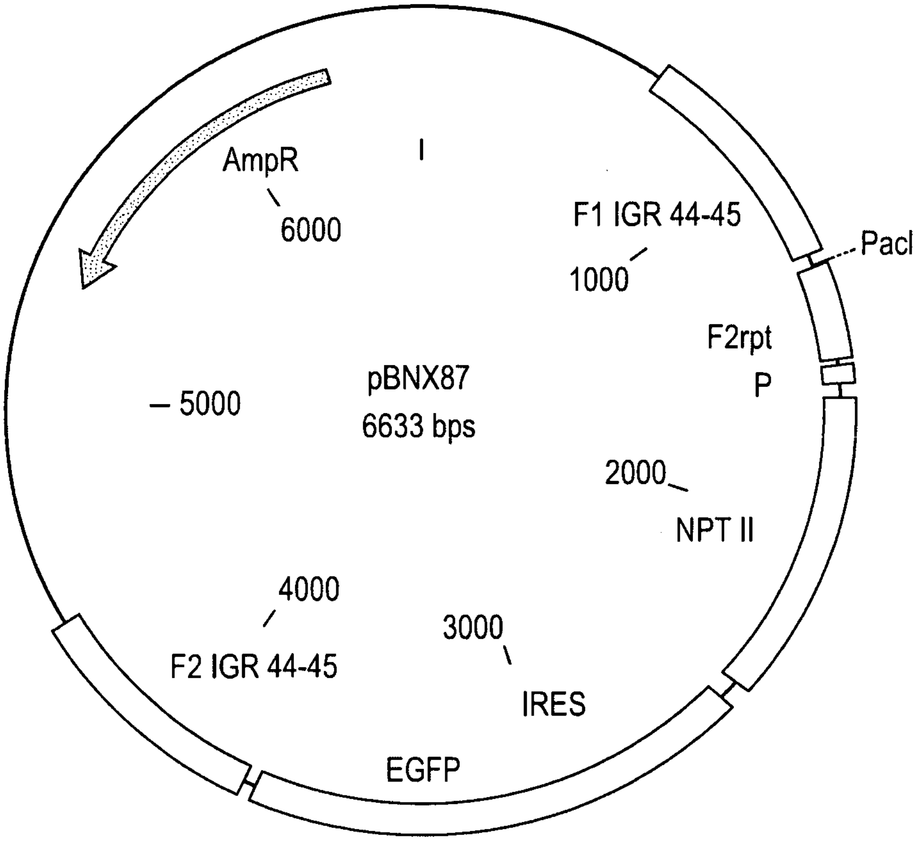

FIG. 11: PCR verification of the recombinant poxvirus including four homologous Dengue virus PrM genes (Example 1). While in the upper part of the gel the different PCR results of the recombinant virus are shown, the lower part provides the results of the same PCR reactions of the control plasmids as indicated. The plasmids containing the homologous sequences are named pBN39, pBN49 or pBN50. PrM stands for the inserted pre-membrane genes of Dengue virus, wherein the numbers indicate from which of the four serotypes it derives. dA=deletion A, dE=deletion E, d2=deletion 2, I4L=intergenic region I4L describes the insertion site of the exogenous DNA.

Figure 18:
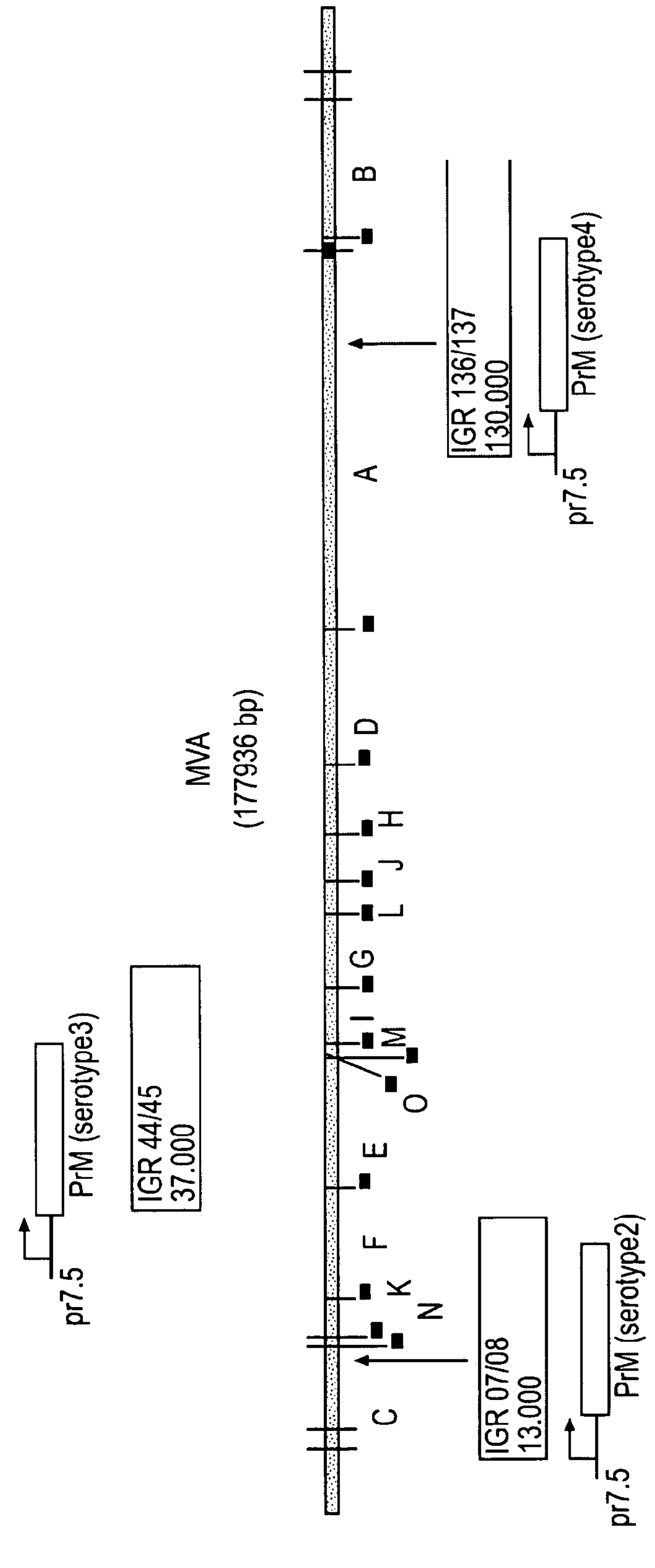

FIG. 18: Schematic presentation of the insertion sites of three PrM genes (serotype 2-4) in the MVA genome according to Example 2.

Figure 19:
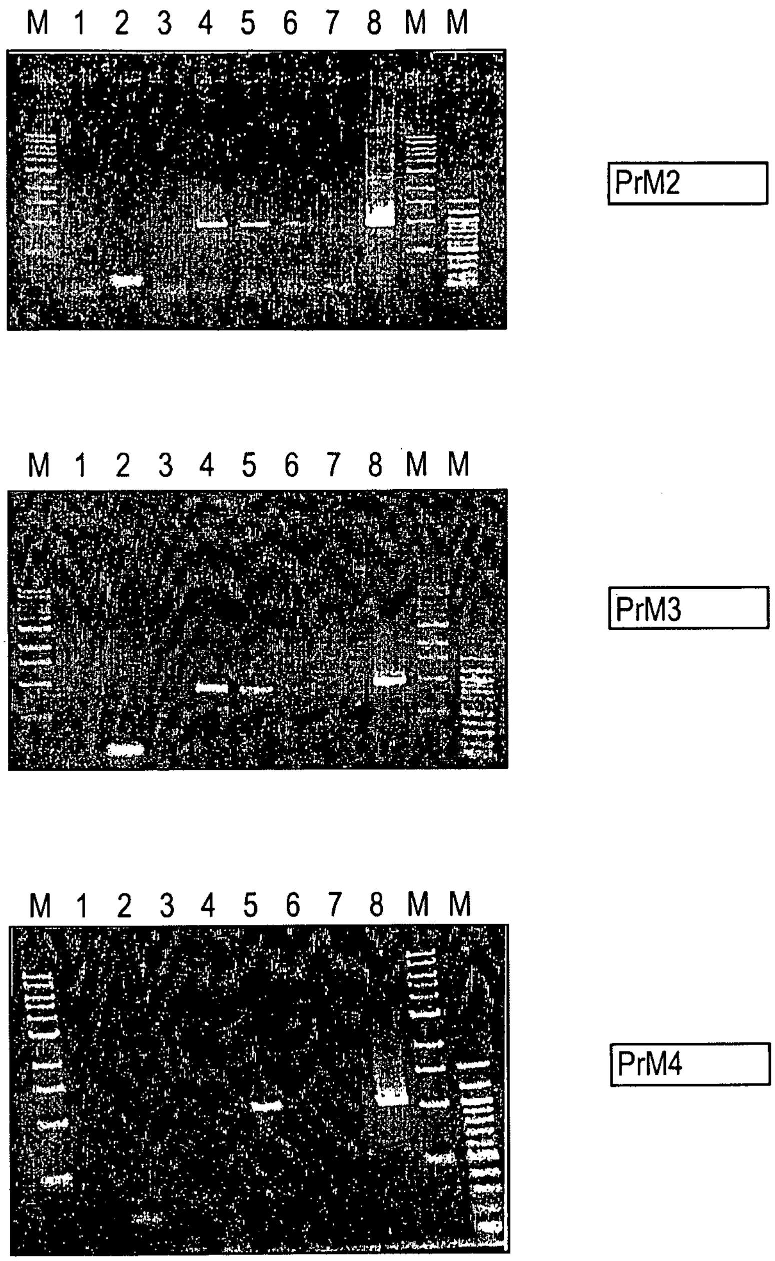

FIG. 19: PCR verification of the recombinant poxvirus including three homologous Dengue virus PrM genes inserted into intergenic regions (Example 2). The upper panel shows the results of the PCR reactions specific for PrM2; the middle panel shows the results of the PCR reactions specific for PrM3, and the lower panel shows the results of the PCR reactions specific for PrM4. Lane 8 shows the same PCR reactions of the control plasmids. Lane 2 shows the empty vector control MVA. PrM stands for the inserted pre-membrane genes of Dengue virus, wherein the numbers indicate from which of the four serotypes it derives. M=Molecular weight marker.

The following examples will further. illustrate the present invention. It will be well understood by a person skilled in the art that the provided examples in no way may be interpreted in a way that limits the applicability of the technology provided by the present invention to this examples.

EXAMPLE 1

Insertion Vectors

Insertion Vector for Deletion A

For the insertion of exogenous sequences into the MVA genome at the so-called deletion A or deletion 1 respectively, corresponding to the genome position 7608-7609, a plasmid vector was constructed, which comprises about 600 bp of the flanking sequences adjacent to the deletion site A. To isolate the flanking sequences from the genomic MVA-BN DNA, suitable PCR primers can be designed with suitable computer software (DNAsis, Hitachi software engineering, San Bruno, USA). Such primers comprise extensions with restriction enzyme sites, which will be used to clone the flanking sequences into a vector plasmid. In between these flanking sequences, a selection gene cassette is introduced, e.g a NPT II gene (neomycin resistance) under the transcriptional control of a poxviral promoter. Additionally, there is a cloning site for the insertion of additional genes or exogenous sequences to be inserted into deletion site A. One such vector construct according to the present invention is disclosed in FIG. 2 (pBNX10).

Insertion Vector for Deletion E

For the insertion of exogenous sequences into the MVA genome at the so-called deletion E or deletion 4, respectively, corresponding with the genome position 170480-170481, a vector was constructed, which comprises about 600 bp of the flanking sequences adjacent to the deletion site E. The vector is designed and constructed like described above. In between the flanking sequences is located an EGFP gene (green fluorescence protein, Clonetech) under the transcriptional control of a poxviral promoter. Additionally, there is a cloning site for the insertion of additional genes or sequences to be inserted into deletion site A. One such vector construct according to the present invention is disclosed in FIG. 3 (pBNX32).

Insertion Vector for Deletion 2

For the insertion of exogenous sequences into the MVA genome at the so-called deletion 2, corresponding with the genome position 20718-20719, a vector was constructed, which comprises about 600 bp of the flanking sequences adjacent to the deletion site 2. The vector is designed and constructed like described above. In between the flanking sequences is located an hbfp gene (humanized blue fluorescing protein, Pavalkis G N et al.) under the transcriptional control of a poxviral promoter. Additionally, there is a cloning site for the insertion of additional genes or sequences to be inserted into deletion site 2. One such vector construct according to the present invention is disclosed in FIG. 4 (pBNX36).

Insertion Vector for Intergenetic Region, I4L

For the insertion of exogenous sequences in the intergenetic region, between the ORF I3L and I4L, corresponding to the genome position 56760, a vector was constructed, which comprises about 600 bp of the flanking sequences adjacent to the intergenetic region at the I4L locus. The vector is designed and constructed like described above. In between the flanking sequences is located an Ecogpt gene (or gpt stands for phosphoribosyltransferase gene isolated from *E. coli*) under the transcriptional control of a poxviral promoter. Additionally, there is a cloning site for the insertion of additional genes or sequences to be inserted into the intergenetic region after the I4L ORF. One such vector construct according to the present invention is disclosed in FIG. 5 (pBNX39).

Construction of Recombinant Poxvirus Comprising Several Homologous Genes Integrated in its Genome.

Insertion Vectors

For the insertion of the four PrM genes of the four serotypes of Dengue virus in the MVA genome four independent recombination vectors were used.

These vectors contain—as described in details above—sequences homologous to the MVA genome for targeting insertion by homologous recombination. Additionally each vector contains a selection—or reporter gene cassette.

The PrM sequences of the four Dengue virus serotypes were synthetically made by oligo annealing and PCR amplification. The PrM sequences were cloned downstream of poxvirus promoter elements to form an expression cassette. This expression cassette was, then, cloned into the cloning site of the relevant insertion vector constructs.

Figure 6:
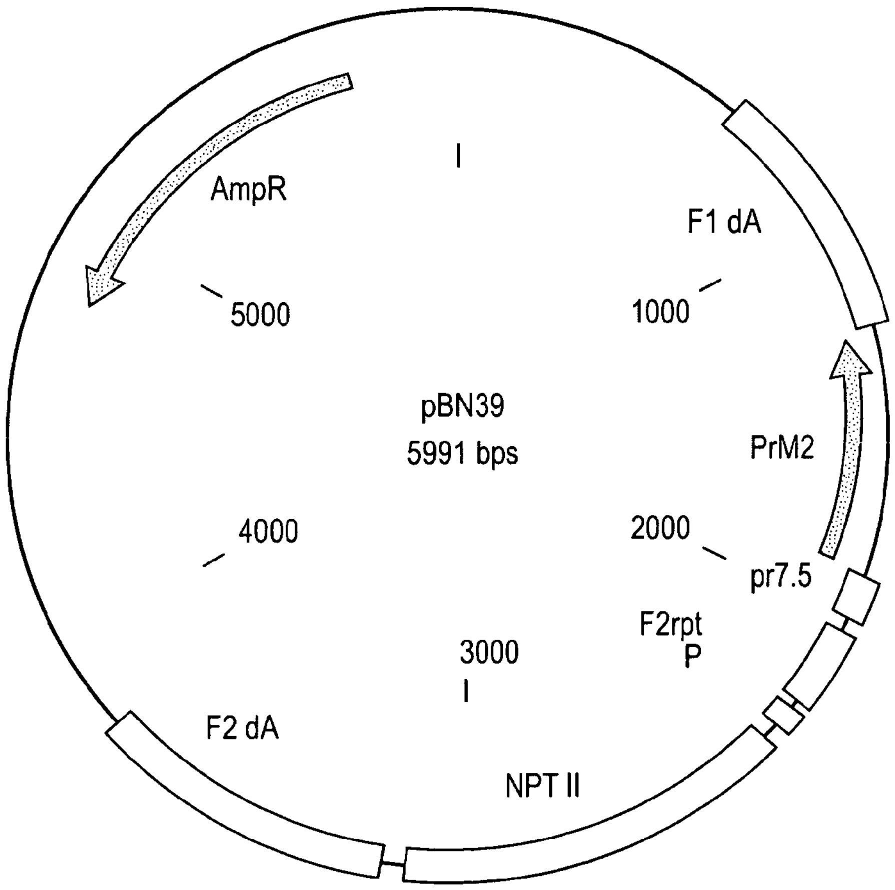
Figure 7:
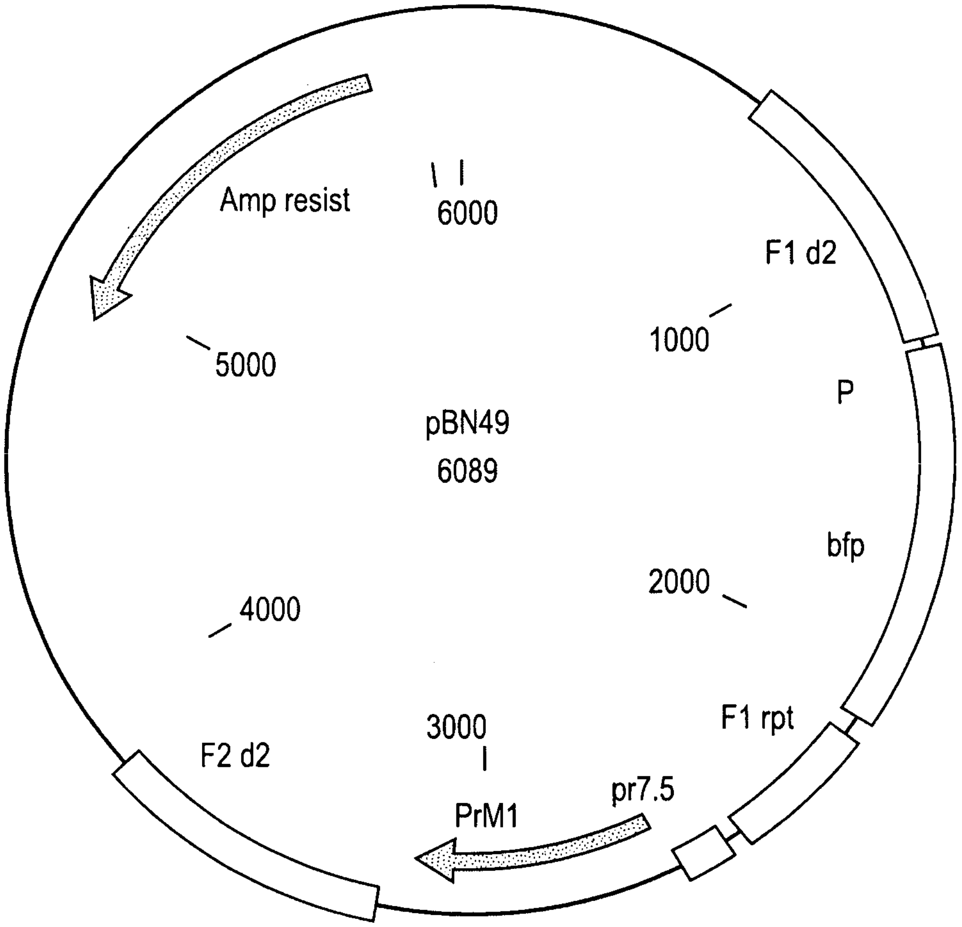
Figure 8:
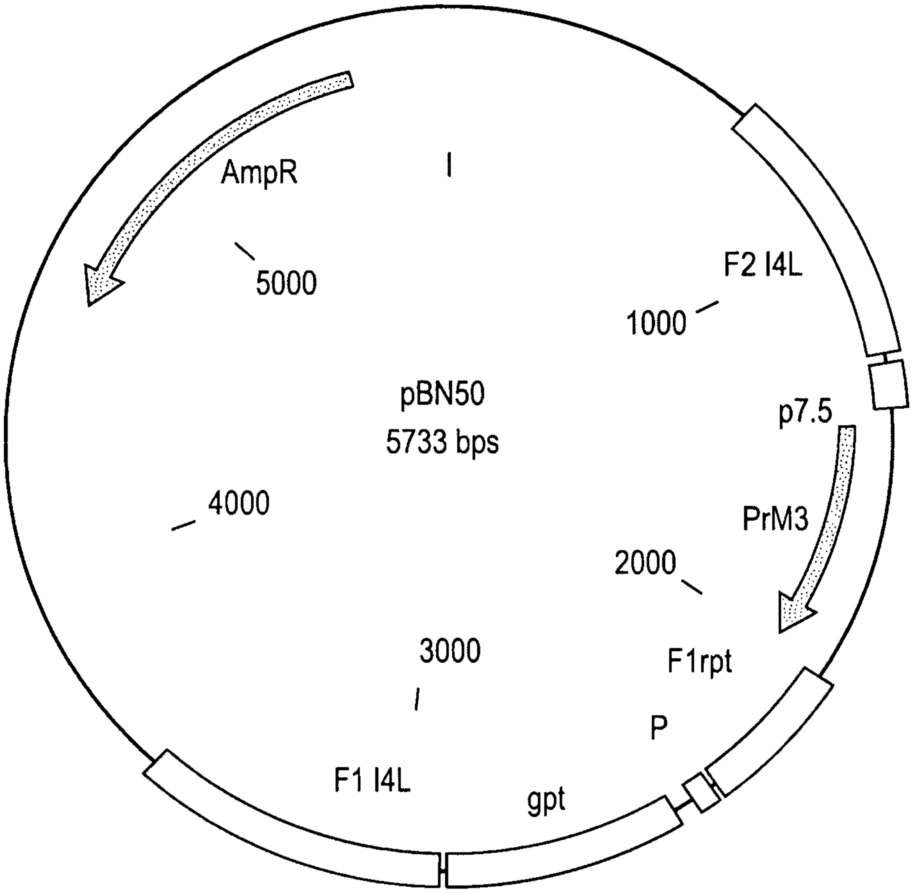
Figure 9:
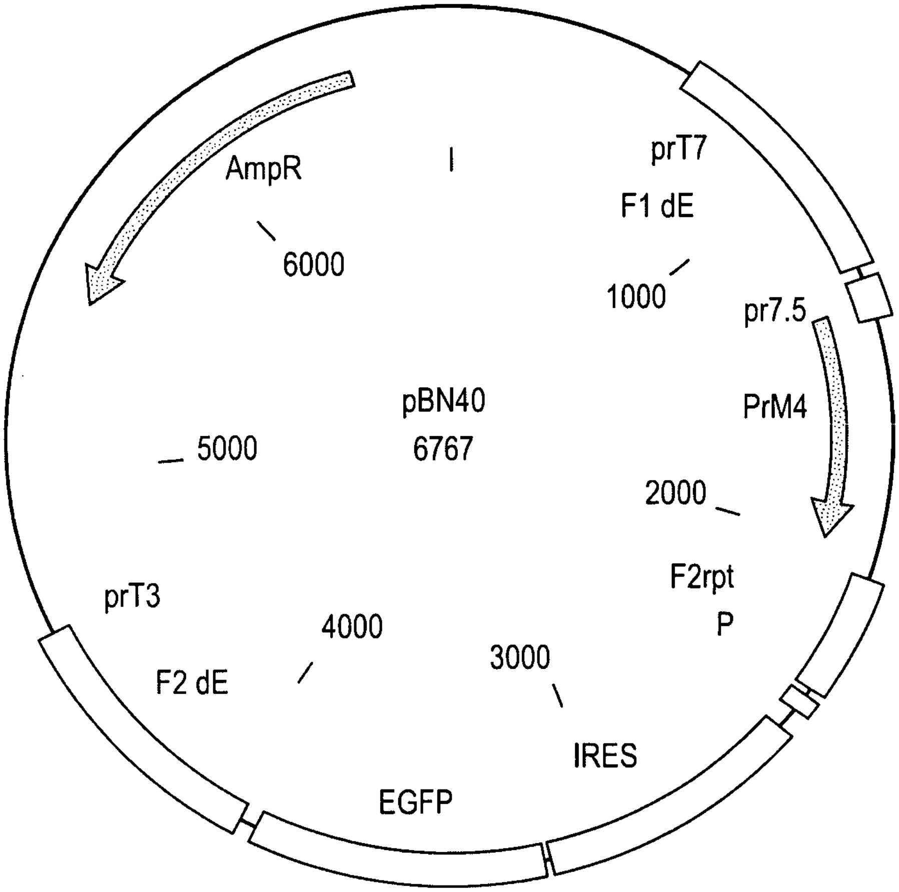

As result, the insertion vector construct for deletion A contained the PrM gene of Dengue virus serotype 2 (FIG. 6—pBN39). The insertion vector construct for deletion 2 contained the PrM gene of Dengue virus serotype 1 (FIG. 7—pBN49). The insertion vector construct for intergenic region I4L contained the PrM gene of Dengue virus serotype 3 (FIG. 8—pBN50). The insertion vector construct for deletion E contained the PrM gene of Dengue virus serotype 4 (FIG. 9—pBN40).

PCR Verification of the Insertion Vectors

For verification of the cloning strategies, PCR assays were performed. For these PCR assays the selected primer pairs are a combination of a primer specifically binding to the specific flanking sequence relative to the insertion site and a second primer specifically binding to one of the highly homologous Dengue virus PrM genes.

The insertion vector for deletion A containing the PrM gene of Dengue virus serotype 2 was screened with the Primers oBN93 (CGCGGATCCATGCTGAACATCTTGAACAGGAGACGCAGA. SEQ ID NO.: 1) and oBN477 (CATGATAAGAGATTGTATCAG. SEQ ID NO.: 2).

The insertion vector for deletion 2 containing the PrM gene of Dengue virus serotype 1 was screened with the Primers oBN194 (ATGTTGAACATAATGAACAGGAGGAAAAGATCTGTGACCATGCTCCTCATGCTGCTGC CCACAGCCCTGGCGTTCCATCT. SEQ ID NO.: 3) and oBN476 (GATTTTGCTATTCAGTGGACTGGATG. SEQ ID NO.: 4).

The insertion vector for intergenic region. I4L containing the PrM gene of Dengue virus serotype 3 was screened with the Primers oBN255 (CCTTAATCGAATTCTCATGTCATGGATGGGGTAACCAGCATTAATAGT. SEQ ID NO.: 5) and oBN479 (GCTCCCATTCAATTCACATTGG. SEQ ID NO.: 6).

The insertion vector for deletion E containing the PrM gene of Dengue virus serotype 4 was screened with the Primers oBN210 (ATCCCATTCCTGAATGTGGTGTTAAAGCTACTGAGCGCTTCTCTCGTCTCCGTTCTCC GCTCTGGGTGCATGTCCCATAC. SEQ ID NO.: 7) and oBN478 (GTACATGGATGATATAGATATG. SEQ ID NO.: 8).

PCR experiments are performed in a Thermal cycler GeneAmp 9700 (Perkin Elmer) using the Taq DNA Polymerase Kit containing 10×PCR buffer, $MgCl_2$ buffer and Taq DNA polymerase (Roche, Cat. no. 201205) or equivalent. In general the PCR reactions were prepared with a total reaction volume of 50 μl containing 45 μl mastermix, the sample DNA and $ddH_2O$ as required. The mastermix should be prepared with 30.75 μl $DdH_2O$, 5 μl 10× buffer, 1 μl dNTP-mix (10 mM each), 2.5 μl of each primer (5 pmol/μl), 3 μl $MgCl_2$ (25 mM) and 0.25 μl Taq-polymerase (5 U/μl).

The amplification was performed using the following programme:

| | | | |
|---|---|---|---|
| 1) | Denaturation: | 4 min | 94° C. |
| 2) | 30 Cycles: | | |
| | Denaturation: | 30 sec | 94° C. |
| | Annealing: | 30 sec | 55° C. |
| | Elongation: | 1-3 min | 72° C. |
| 3) | Elongation | 7 min | 72° C. |
| 4) | Store | | 4° C. |

Based on the size of the inserted gene the elongation time should at least be 1 min/kb.

The PCR results shown in FIG. 10 demonstrate the specificity of the primer combinations used for the single insertions.

The primer combination oBN194/oBN476 is specific for deletion 2 and PrM1 as insert. The expected PCR fragment of plasmid pBN49 has a size of 678 bp (shown in lane 3, upper part of the gel).

The primer combination oBN255/oBN479 is specific for intergenic region I4L and PrM3 as insert. The expected PCR fragment of plasmid pBN50 has a size of 825 bp (shown in lane 9, upper part of the gel).

The primer combination oBN210/oBN478 is specific for deletion E and PrM4 as insert. The expected PCR fragment of plasmid pBN40 has a size of 607 bp (shown in lane 5, lower part of the gel).

The primer combination oBN93/oBN477 is specific for deletion A and PrM2 as insert. The expected PCR fragment of plasmid pBN39 has a size of 636 bp (shown in lane 11, lower part of the gel).

Generation of the Recombinant MVA Via Homologous Recombination

For expression of foreign genes by a recombinant MVA, these genes have to be inserted into the viral genome by a process called homologous recombination. For that purpose, the foreign gene of interest had been cloned into an insertion vector, as described above. This vector has to be transfected after infection of cells with MVA-BN. The recombination will take place in the cellular cytoplasm of the infected and transfected cells. With help of the selection and/or reporter cassette, which is also contained in the insertion vector, cells comprising recombinant viruses are identified and isolated.

Homologous Recombination

For homologous recombination, BHK (Baby hamster kidney) cells or CEF (primary chicken embryo fibroblasts) cells are seeded in 6 well plates using DMEM (Dulbecco's Modified Eagles Medium, Gibco BRL)+10% fetal calf serum (FCS) or VP-SFM (Gibco BRL)+4 mmol/l L-Glutamine for a serum free production process.

Cells need to be still in the growing phase and, therefore, should reach 60-80% confluence on the day of transfection. Cells were counted before seeding, as the number of cells has to be known for determination of the multiplicity of infection (moi) for infection.

For infection, the MVA stock is diluted in DMEM/FCS or VP-SFM/L-Glutamine so that 500 μl dilution contain an appropriate amount of virus that will give a moi of 0.01. Cells are assumed to be divided once after seeding. The medium is removed from cells and cells are infected with 500 μl of diluted virus for 1 hour rocking at room temperature. The inoculum is removed and cells are washed with DMEM/VP-SFM. Infected cells are left in 1.6 ml DMEM/FCS and VP-SFM/L-Glutamine respectively while setting up transfection reaction (Qiagen Effectene Kit).

For transfection, the "Effectene" transfection kit (Qiagen) is used. A transfection mix is prepared of 1-5 μg of linearized insertion vector (total amount for multiple transfection) with buffer EC to give a final volume of 150 μl. Add 8.0 μl Enhancer per μg DNA, vortex and incubate at room temperature for 5 min. Then, 25 μl of Effectene are added per μg DNA after vortexing stock tube and the solution is mixed thoroughly by vortexing and incubated at room temperature for 10 min. 600 μl of DMEM/FCS and VP-SFM/L-Glutamine respectively, are added, mixed and subsequently, the whole transfection mix is added to the cells, which are already covered with medium. Gently the dish is rocked to mix the transfection reaction. Incubation takes place at 37° C. with 5% $CO_2$ over night. The next day the medium is removed and replaced with fresh DMEM/FCS or VP-SFM/L-Glutamine. Incubation is continued until day 3.

For harvesting, the cells are scraped into medium, then the cell suspension is transferred to an adequate tube and frozen at −20° C. for short-term storage or at −80° C. for long term storage.

Insertion of PrM4 into MVA

In a first round, cells were infected with MVA-BN according to the above-described protocol and were additionally transfected with insertion vector pBN40 containing the PrM gene of Dengue virus serotype 4 and as reporter gene the EGFP gene. Since the transfected vector contains a reporter gene, EGFP, the synthesized protein is detectable latest on day three in cells infected with a recombinant virus. Resulting recombinant viruses have to be purified by plaque purification.

For plaque purification infected cells (fluorescing or stained) are isolated with a pipet tip, resuspended and aspirated in 200 μl PBS or medium. Then a fresh culture dish containing about 10E6 cells is infected with 100 μl of the resuspended plaques. After 48 h cells are taken up in 300 μl PBS. DNA is extracted from suspension and screened with PCR analysis. A clone that shows the expected bands is chosen and fresh 6-well plates are infected with different amounts of this virus. Overlaying the wells with 1% agarose avoids further spreading of virus. After 48 h infected cells comprising a recombinant virus clone are isolated.

This procedure is repeated until no wild-type MVA-BN can be detected in the PCR analysis.

After 4 rounds of plaque purification recombinant viruses, MVA-PrM4, were identified by PCR assays using a primer pair selectively amplifying the expected insertion (oBN210 and oBN478, as described above) and as control a primer pair specifically recognizing the insertion site deletion E (oBN453: GTTGAAGGATTCACTTCCGTGGA, SEQ ID NO.: 9 and oBN454: GCATTCACAGATTCTATTGTGAGTC, SEQ ID NO.: 10)

Insertion of PrM2 into MVA-PrM4

Cells were infected with MVA-PrM4 according to the above described protocol and were additionally transfected with insertion vector pBN39 containing the PrM gene of Dengue virus serotype 2 and as selection gene the NPT II, a neomycin resistance gene. For purification of recombinant MVA expressing an antibiotic resistance gene three rounds of virus amplification under selective conditions before plaque purification are recommended. For neomycinphosphotransferase selection G418 is added to the medium. G418 is a derivative of neomycin and inhibits the protein-biosynthesis by interference with the action of the ribosomes. NPT gene activity inactivates G418 bp phosphorylation.

After 16 rounds of plaque purification under neomycin selection recombinant viruses, MVA-PrM4/PrM2, were identified by PCR assays using a primer pair selectively amplifying the expected insertion (oBN93 and oBN477, as described above) and as control a primer pair specifically recognizing the insertion site deletion A (oBN477: as described above) and oBN452: GTTTCATCAGAAATGACTCCATGAAA, SEQ ID NO.: 11). Additionally also insertion of PrM4 into deletion E is verified with the primer pairs: oBN210-oBN478 and oBN453-oBN454.

Insertion of PrM1 into MVA

In a first round, cells were infected with MVA-BN according to the above described protocol and were additionally transfected with insertion vector pBN49 containing the PrM gene of Dengue virus serotype 1 and as reporter gene the hbfp, the gene for humanized blue fluorescing protein. The synthesized hbfp protein is detectable on day three in cells infected with a recombinant virus. Resulting recombinant viruses were purified by plaque purification.

After 10 rounds of plaque purification recombinant viruses, MVA-PrM1, were identified by PCR assays using a primer pair selectively amplifying the expected insertion (oBN194 and oBN476, as described above) and as control a primer pair specifically recognizing the insertion site deletion 2 (oBN54: CGGGGTACCCGACGAACAAGGAACTGTAGCAGAGGCATC, SEQ ID NO.: 12 and oBN56: AACTGCAGTTGTTCGTATGTCATAAATTCTTTAATTAT, SEQ ID NO.: 13)

Insertion of PrM3 into MVA

In a first round, cells were infected with MVA-BN according to the above described protocol and were additionally transfected with insertion vector pBN50 containing the PrM gene of Dengue virus serotype 3 and as reporter gene the Ecogpt gene (Ecogpt or shortened to gpt stands for phosphoribosyltransferase gene). Resulting recombinant viruses were purified by 3 rounds of plaque purification under phosphoribosyltransferase metabolism selection by addition of mycophenolic acid, xanthin and hypoxanthin. Mycophenolic acid (MPA) inhibits inosine monophosphate dehydrogenase and results in blockage of purine synthesis and inhibition of viral replication in most cell lines. This blockage can be overcome by expressing Ecogpt from a constitutive promoter and providing the substrates xanthine and hypoxanthine.

Resulting recombinant viruses, MVA-PrM3, were identified by PCR assays using a primer pair selectively amplifying the expected insertion (oBN255 and oBN479, as described above) and as control a primer pair specifically recognizing the insertion site I4L (oBN499: CAACTCTCTTCTTGATTACC, SEQ ID NO.: 14 and oBN500: CGATCAAAGTCAATCTATG; SEQ ID NO.: 15).

Coinfection of MVA-PrM1 and MVA-PrM3

The cells were infected with equal amounts of MVA-PrM1 and MVA-PrM3 according to the above protocol. After 3 rounds of plaque purification under phosphoribosyltransferase metabolism selection of blue fluorescing clones of recombinant viruses were analyzed by PCR using the primer pairs (oBN255 and oBN479. oBN499 and oBN500. oBN194 and oBN476. oBN54 and oBN56 as described above). Resulting recombinant viruses were designated MVA-PrM1/PrM3.

Coinfection of MVA-PrM1/PrM3 and MVA-PrM2/PrM4

The cells were infected with equal amounts of MVA-PrM1/PrM3 and MVA-PrM2/PrM4 according to the above protocol. Plaque purification was performed under phosphoribosyltransferase metabolism and neomycin selection. Recombinant viruses inducing a green and blue fluorescence were isolated and analyzed by PCR using the primer pairs (oBN255 and oBN479. oBN499 and oBN500. oBN194 and oBN476. oBN54 and oBN56. oBN93 and oBN477. oBN477 and oBN452. oBN210 and oBN478. oBN453 and oBN454 as described above).

The PCR analysis of the recombinant virus (Clone 20) comprising all four PrM genes is shown in FIG. 11. While in the upper part of the gel the different PCR results of the recombinant virus are shown, the lower part provides the results of the same PCR reactions of the control plasmids (as indicated). Lane 1, 10 and 11 show a 1 kb and a 100 bp molecular marker.

The primer combination oBN210/oBN478 is specific for deletion E and PrM4 as insert. The expected PCR fragment of the recombinant virus and the plasmid pBN40 has a size of 607 bp (shown in lane 2).

The primer combination oBN453/oBN454 is specific for deletion E. The expected PCR fragment of the recombinant virus is 2.7 kb, the expected band of the wild-type virus 2.3 kb (shown in lane 3). Also in the upper part of the gel a band specific for a wild-type virus can be identified. This means that the recombinant virus preparation is not yet completely free of wild-type virus. Further plaque purification is necessary.

The primer combination oBN93/oBN477 is specific for deletion A and PrM2 as insert. The expected PCR fragment of the recombinant virus and the plasmid pBN39 has a size of 636 bp (shown in lane 4).

The primer combination oBN477/oBN452 is specific for deletion A. The expected PCR fragment of the recombinant virus is 4.1 kb, the expected band of the wild-type virus 2.7 kb (shown in lane 5). In the upper part of the gel a band specific for a wild-type virus can be identified.

The primer combination oBN255/oBN479 is specific for intergenic region I4L and PrM3 as insert. The expected PCR fragment of the recombinant virus and the plasmid pBN50 has a size of 825 bp (shown in lane 6).

The primer combination oBN499/oBN500 is specific for the intergenic region of I4L. The expected PCR fragment of the recombinant virus is 1.0 kb, the expected band of the wild-type virus 0.3 kb (shown in lane 7).

The primer combination oBN194/oBN476 is specific for deletion 2 and PrM1 as insert. The expected PCR fragment of the recombinant virus and the plasmid pBN49 has a size of 678 bp (shown in lane 8).

The primer combination oBN54/oBN56 is specific for deletion 2. The expected PCR fragment of the recombinant virus is 1.6 kb, the expected band of the wild-type virus 0.9 kb (shown in lane 9). In the upper part of the gel a band specific for a wild-type virus can be identified.

Alternatively, one can produce 4 different viruses, coinfect cells with all four viruses and screen for a recombinant.

Improvements can also be achieved with recombination vectors, which contain further selection- or resistance markers.

EXAMPLE 2

Insertion Vectors

Recombination Vector for Intergenic Region 136-137 (IGR 136-137)

For the insertion of exogenous sequences into the MVA genome at the so-called intergenic region (IGR) 136-137 corresponding to the genome position 129.940 a plasmid vector was constructed which comprises about 600 bp of the flanking sequences adjacent to the insertion site. To isolate the flanking sequences from the genomic MVA-BN DNA suitable PCR primers can be designed. Such primers comprise extensions with restriction enzyme sites, which will be used to clone the flanking sequences into a vector plasmid. In between this flanking sequences, a selection gene cassette is introduced, e.g. NPT II gene (neomycine resistance) under the transcriptional control of a poxviral promoter (P). Additionally there is a cloning site for the insertion of additional genes or exogenous sequences to be inserted into IGR 136-137 (PacI). One such vector construct according to the present invention is disclosed in FIG. 12 (pBNX67).

Recombination Vector for Intergenic Region 07-08 (IGR 07-08)

For the insertion of exogenous sequences into the MVA genome in the intergenic region (IGR) 07-08 corresponding to the genome position 12.800, a plasmid vector was constructed which comprises about 600 bp of the flanking sequences adjacent to the insertion site. To isolate the flanking sequences from the genomic MVA-BN DNA suitable PCR primers can be designed. Such primers comprise extensions with restriction enzyme sites, which will be used to clone the flanking sequences into a vector plasmid. In between this flanking sequences, a selection gene cassette is introduced, e.g., Ecogpt gene (Guanin-Phosphoribosyltransferase) under the transcriptional control of a poxviral promoter (P). Additionally, there is a cloning site for the insertion of additional genes or exogenous sequences to be inserted into IGR 07-08 (PacI). One such vector construct according to the present invention is disclosed in FIG. 13 (pBNX88).

Recombination Vector for Intergenic Region 44-45 (IGR 44-45)

For the insertion of exogenous sequences into the MVA genome at the intergenic region (IGR) 44-45 corresponding to the genome position 37.330, a plasmid vector was constructed which comprises about 600 bp of the flanking sequences adjacent to the insertion site. To isolate the flanking sequences from the genomic MVA-BN DNA suitable PCR primers can be designed. Such primers comprise extensions with restriction enzyme sites, which will be used to clone the flanking sequences into a vector plasmid. In between this flanking sequences, a selection gene cassette is introduced, e.g., NPT II gene (neomycine resistance) under the transcriptional control of a poxviral promoter (P). Additionally there is a cloning site for the insertion of additional genes or exogenous sequences to be inserted into IGR 44-45 (PacI). One such vector construct according to the present invention is disclosed in FIG. 14 (pBNX87).

Construction of Recombinant Poxvirus Comprising Several Homologous Genes Integrated in its Genome Insertion Vectors For the insertion of the three PrM genes of serotype 2, 3 and 4 of Dengue virus in the MVA genome, three independent recombination vectors were used.

These vectors contain—as described in detail above—sequences homologous to the MVA genome for targeting insertion by homologous recombination. Additionally each vector contains a selection and reporter gene cassette.

The PrM sequences of three Dengue virus serotypes were synthetically made as described in Example 1.

Figure 15:
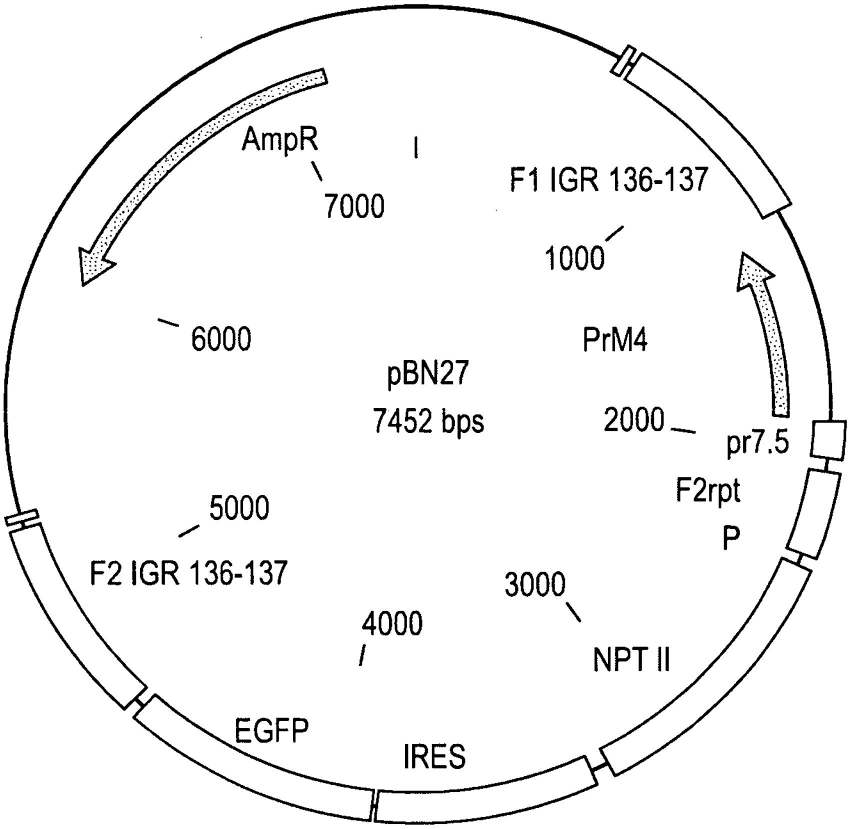
Figure 16:
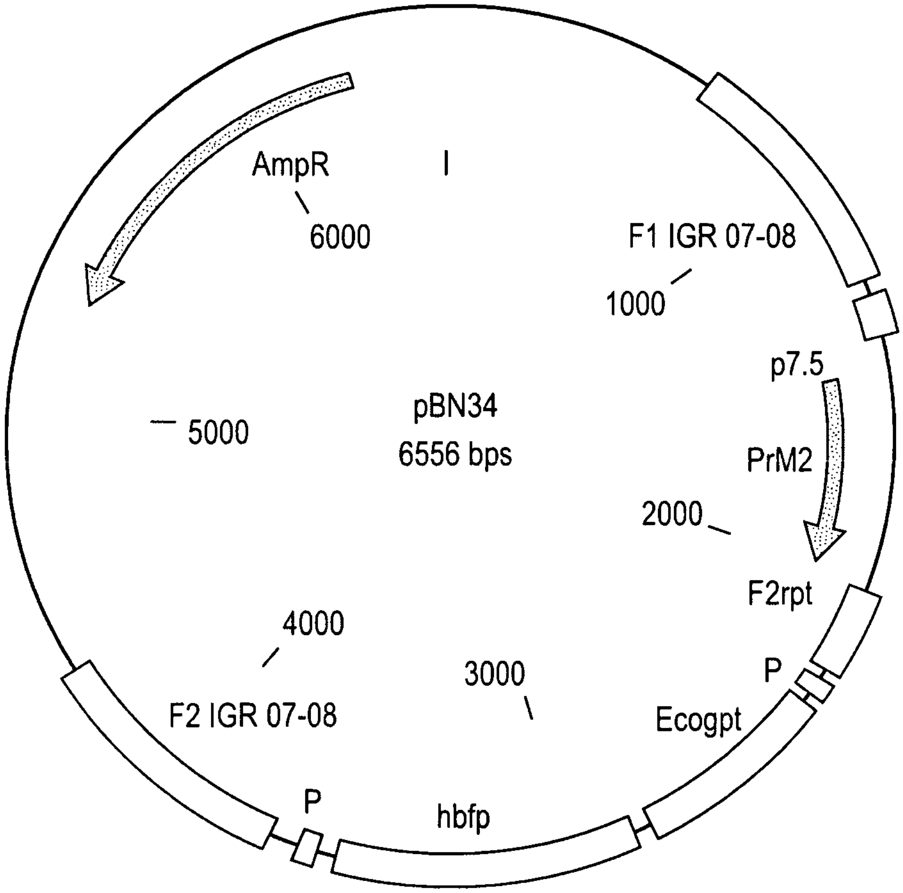
Figure 17:
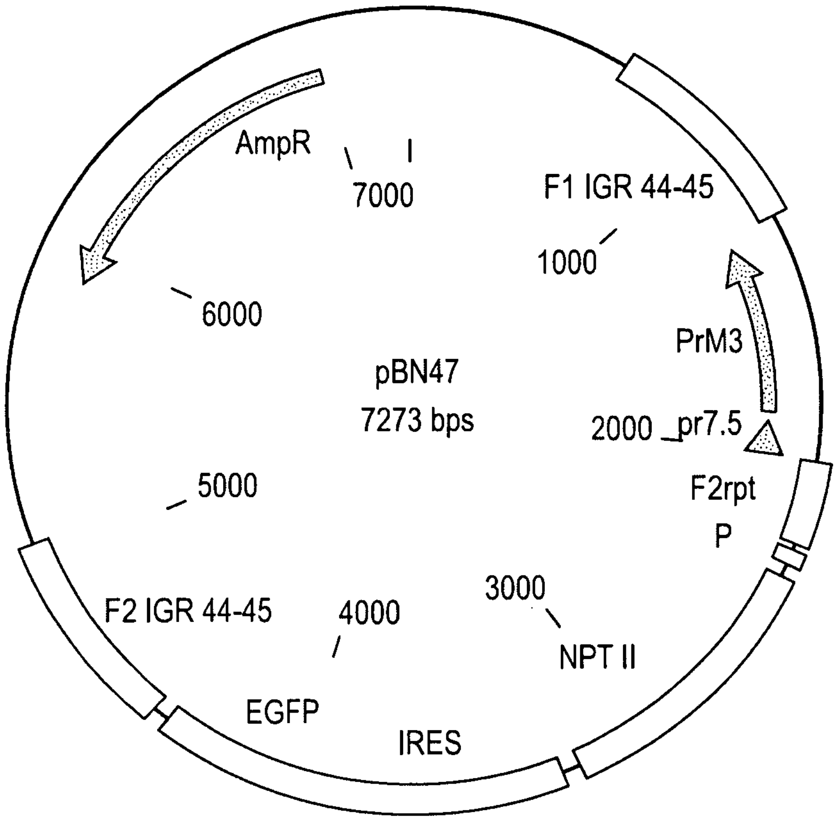

As result, the insertion vector construct for IGR136-137 contained the PrM of Dengue virus serotype 4 (FIG. 15—pBN27). The insertion vector construct for IGR 07-08 contained the PrM of Dengue virus serotype 2 (FIG. 16—pBN34), and the insertion vector construct for IGR 44-45 contained the PrM of Dengue virus serotype 3 (FIG. 17—pBN47).

Generation of the Recombinant MVA Via Homologous Recombination

The generation of recombinant MVA by homologous recombination was performed as described in Example 1.

The insertion sites for the PrM4, PrM3 and PrM 2 in the MVA genome are depicted in FIG. 18.

Insertion of PrM 4 into MVA

In a first round, cells were infected with MVA-BN according to the above-described protocol and were additionally transfected with the insertion vector pBN27 containing the PrM gene of Dengue virus serotype 4 and as a reporter gene the EGFP gene. Since the transfected vector contains a reporter gene, EGFP, the synthesized protein is detectable latest on day three in cells infected with a recombinant virus. Resulting recombinant viruses have to be purified by plaque purification as described in Example 1. After four rounds of plaque purification recombinant viruses, MVA-PrM4, were identified by PCR assays using a primer pair selectively amplifying the insertion site IGR136-137 (oBN1008: gataccgatcacgttcta. SEQ ID NO.: 16; and oBN1009 ggatatgattatgtagag. SEQ ID NO.: 17).

Insertion of PrM 2 into MVA

Cells were infected with MVA-PrM4 according to the above-described protocol and were additionally. transfected with the insertion vector pBN34 containing the PrM gene of Dengue virus serotype 2 and as a reporter gene the BFP gene. Since the transfected vector contains a reporter gene, BFP, the synthesized protein is detectable latest on day three in cells infected with a recombinant virus. Resulting recombinant viruses have to be purified by plaque purification as described in Example 1. After six rounds of plaque purification recombinant virus MVA-PrM4+PrM2 was further passaged and amplified and a crude stock was prepared. The recombinant was identified by PCR assays using a primer pair selectively amplifying the insertion site IGR07-08 (oBN 903: ctggataaatacgaggacgtg. SEQ ID NO.: 18; and oBN904: gacaattatccgacgcaccg; SEQ ID NO.: 19).

Insertion of PrM 3 into MVA

Cells were infected with MVA-PrM2+4 according to the above-described protocol and were additionally transfected with the insertion vector pBN47 containing the PrM gene of Dengue virus serotype 3 and as a reporter gene the EGFP gene. Since the transfected vector contains a reporter gene, EGFP, the synthesized protein is detectable latest on day three in cells infected with a recombinant virus. Resulting recombinant viruses have to be purified by plaque purification as described in Example 1. After three rounds of plaque purification recombinant viruses, MVA-PrM4+3+2, were identified by PCR assays using a primer pair selectively amplifying the insertion site IGR44-45 (oBN904: cgttagacaacacaccgacgatgg. SEQ ID NO.: 20; and oBN905 cggatgaaaaatttttggaag. SEQ ID NO.: 21).

The PCR analysis of the recombinant virus comprising the three Dengue virus PrM genes is shown in FIG. 19. PCR experiments are performed as described in Example 1. The primer combination oBN1008 and oBN1009 is specific for IGR136-137, which contains the PrM4 insertion (FIG. 19, lower panel). The expected PCR fragment of the recombinant virus has a size of 1 kb (shown in lane 4, 5 and 6) as the plasmid positive control (lane 8). The empty vector control, devoid of PrM 4 shows the expected fragment of 190 bp (lane 2). Lane M shows the molecular weight marker and lanes 1, 3 and 7 are empty. The primer combination oBN902 and oBN903 is specific for IGR07-08, which contains the PrM2 insertion (FIG. 19, upper panel). The expected PCR fragment of the recombinant virus has a size of 960 bp (shown in lane 4-6) as the plasmid positive control (lane 8). The empty vector control, devoid of PrM 2 shows the expected fragment of 190 bp (lane 2). The primer combination oBN904 and oBN905 is specific for IGR44-45, which contains the PrM3 insertion (FIG. 19, middle panel). The expected PCR fragment of the recombinant virus has a size of 932 bp (shown in lane 4-6) as the plasmid positive control (lane 8). The empty vector control, devoid of PrM 2 shows the expected fragment of 185 bp (lane 2).

What is claimed is:

1. A recombinant MVA comprising at least two foreign genes of greater than 300 nucleotides which are 50-75% homologous in comparison to each other, wherein each of the foreign genes is stably inserted into a different site in the MVA genome.

2. The recombinant MVA of claim 1, wherein at least one of the foreign genes is inserted into an intergenic region.

3. The recombinant MVA of claim 2, wherein the intergenic region is IGR44/45.

4. The recombinant MVA of claim 2, wherein the intergenic region is IGR136/137.

5. The recombinant MVA of claim 2, wherein the intergenic region is IGR07/08.

6. The recombinant MVA of claim 2, wherein the intergenic region is IGR I4L.

7. The recombinant MVA of claim 1, wherein at least one of the foreign genes is inserted into a naturally-occurring deletion site.

8. The recombinant MVA of claim 7, wherein the naturally-occurring deletion site is deletion site 1.

9. The recombinant MVA of claim 7, wherein the naturally-occurring deletion site is deletion site 2.

10. The recombinant MVA of claim 7, wherein the naturally-occurring deletion site is deletion site 4.

11. The recombinant MVA of claim 1, wherein the two foreign genes are 65-75% homologous in comparison to each other.

12. The recombinant MVA of claim 1, wherein the foreign genes are *flavivirus* genes.

13. The recombinant MVA of claim 12, wherein the *flavivirus* is a Dengue virus.

14. The recombinant MVA of claim 12, wherein the foreign genes are Dengue virus PrM genes.

15. The recombinant MVA of claim 12, wherein one of the foreign genes is a Dengue virus serotype 1 gene.

16. The recombinant MVA of claim 12, wherein one of the foreign genes is a Dengue virus serotype 2 gene.

17. The recombinant MVA of claim 12, wherein one of the foreign genes is a Dengue virus serotype 4 gene.

18. The recombinant MVA of claim 14, wherein one of the foreign genes is a Dengue virus serotype 1 gene.

19. The recombinant MVA of claim 14, wherein one of the foreign genes is a Dengue virus serotype 2 gene.

20. The recombinant MVA of claim 14, wherein one of the foreign genes is a Dengue virus serotype 4 gene.

21. The recombinant MVA of claim 1, wherein the MVA contains only two foreign genes of greater than 300 nucleotides which are 50-75% homologous in comparison to each other.

22. The recombinant MVA of claim 1, wherein the MVA contains only three foreign genes of greater than 300 nucleotides which are 50-75% homologous in comparison to each other.

* * * * *